United States Patent [19]

Spencer et al.

[11] 3,947,434

[45] Mar. 30, 1976

[54] 9-(p-PHENYLAZOANILINO)-7-METHYL-1H-IMIDAZO[4,5-f]QUINOLINES

[75] Inventors: Claude F. Spencer; Harry R. Snyder, Jr., both of Norwich, N.Y.

[73] Assignee: Morton-Norwich Products, Inc., Norwich, N.Y.

[22] Filed: Mar. 26, 1975

[21] Appl. No.: 562,172

Related U.S. Application Data

[62] Division of Ser. No. 367,501, June 6, 1973, Pat. No. 3,919,238.

[52] U.S. Cl. ............................ 260/155; 424/226
[51] Int. Cl.² ........................................ C07C 107/06

[58] Field of Search ................. 260/155; 424/226

[56] References Cited
UNITED STATES PATENTS
2,245,262  6/1941  Dickey et al. ...................... 260/155

*Primary Examiner*—Charles F. Warren
*Attorney, Agent, or Firm*—Anthony J. Franze

[57] ABSTRACT

A series of 9-(substituted amino)imidazo[4,5-f]quinolines are effective anthelmintic agents; particularly in respect to the tapeworm Hymenolepis nana.

1 Claim, No Drawings

9-(P-PHENYLAZOANILINO)-7-METHYL-1H-IMIDAZO[4,5-f]QUINOLINES

This is a division of application Ser. No. 367,501, filed June 6, 1973, now U.S. Pat. No. 3,919,238, issued Nov. 11, 1975.

This invention relates to chemical compounds; particularly a series of 9(substituted amino)imidazo[4,5-f]quinolines of the formula:

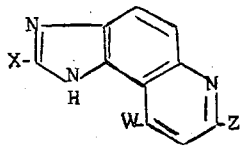

(I)

wherein X is hydrogen, methyl, phenyl or hydroxy;
Z is methyl, ethyl, hydrogen or phenyl;
W is 2-piperidino-5-pyridylamino,[6-(4-methyl-1-piperazinyl)-3-pyridyl]amino, (4-methoxybenzyl)amino, 2-methoxy-5-pyridylamino, β-naphthylamino, cyclohexylamino, α-naphthylamino, anilino or-HN-

wherein R is 4-methyl, 2-chloro-5-methyl, 4-butyl, 3-chloro-4-methyl, 4sec. butyl, 3-trifluoromethyl, 3-trifluoromethyl-4-chloro, 2-phenyl, 4-phenyl, 2-methyl-3-chloro, 4-isopropyl, 3,4-dichloro, 4-bromo, 4-iodo, 4-dimethylamino, 4-diethylamino, 3-chloro-4-dimethylamino, 4-piperidino, 4-(4-methylpiperazinyl), 3-dimethylamino, 3-chloro-4-piperidino, 3-chloro-4-(4-methyl)piperazinyl, 3chloro-4-(4-benxyl) piperazinyl, 4-methoxy, 4-ethoxy, 2-methoxy, 3-chloro-4-ethoxy, 4-butoxy, 3-methoxy, 4-phenoxy, 4-methylthio, 4-benzyloxy, 2-methylthio, 3-methylthio, 3,4-dimethoxy, 3,4-diethoxy, 3,4-diisopropoxy, 3,4diisobutoxy, 3,4-dibutoxy, 3,4-disec. amyloxy, 2,5-diethoxy, 2,5-dimethoxy, 2,5-dimethoxy-4-chloro, 2-ethoxy-5-methoxy, 2-methoxy-5-ethoxy, 2,5-diethoxy-4-chloro, 2,4-dimethoxy-5-chloro, 3,4,5-trimethoxy, 2,4,5-triethoxy, 4-acetyl, 3-acetyl, 4-propionyl, 4-butyryl, 2-methyl-4-chloro, 3-nitro-4-methyl, 3-chloro-4-ethyl, 3-chloro-4-butyl, 3-chloro-4fluro, 3-chloro-4-pyrrolidino, 4-phenylazo, 2-methoxy-4-chloro, 3,4-methylenedioxy, 3,4-diamyloxy, 3,4-diisoamyloxy, 4-chloro-2,5-dibutoxy, or 4-(2-diethylamino)ethoxy.

The members of this series of 9-(substitued amino)imidazo[4,5-f] quinolines are effective anthelmintic agents. When administered perorally to mice harboring the intestinal tapeworm, Hymenolepis nana, as an aqueous suspension, conveniently, if desired, prepared using a suspending agent such as sodium alginate, clearance of from 40–100% of that intestinal parasite is accomplished. Hymenolepis nana is frequently found in the human intestine.

The methods by which members of the series of this invention are prepared are illustrated in the following examples in which the compounds are usually obtained as the hydrochloride salt. These methods consist in reacting a 9-chloroimidazo[4,5-f]quinoline with a pyridylamine, naphthylamine, benzylamine, cyclohexylamine or an aniline.

Example I

9-Anilino-7methyl-1H-imidazo[4,5-f]quinoline Hydrochloride

A. Ethyl 3-(5-Benzimidazolylamino)crotonate

An 82 g. (0.5 mole) sample of 5-nitrobenzimidazole in 900 ml of ethanol was reduced over 4 g. of 5% Pd/C catalyst containing 50% $H_2O$. After a pressure drop of 108 lb. (calcd. 106 lb.), the reduction stopped. After filtration of the catalyst, 65 g. (0.5 mole) of ethyl acetoacetate, 20 g. of anhydrous calcium sulfate, and 0.5 ml of HOAc was added. After filtration of the anhydrous calcium sulfate the solution was concentrated in vacuo till till a solid remained. The product was filtered and washed with fresh ethanol and air-dried. The yield was 84 g. (69%), m.p. 160°–162°C.

B. 7-Methyl-9-imidazo[4,5-f]quinolinol 40 g. of A. was added to 800 ml. of boiling Dowtherm and the boiling was continued for 6 minutes. The product separated upon cooling. The product was filtered, washed with Dowtherm and then acetone and air-dried. The yield was 29 g. (91%), m.p. 345°–347°C.

C. 9-Chloro-7-methyl-1H-imidazo[4,5-f]quinoline

A suspension of 4.0 g. of B. in 100 ml. of phosphorus oxychloride was heated under reflux for 45 min. and then allowed to cool. The solid was filtered, washed with benzene, air-dried briefly and then dissolved in 100 ml. of water. The cloudy solution was filtered and, after addition of crushed ice, was made alkaline with ammonium hydroxide. The oily product which separated began to crystallize in a short time. It was filtered, washed with water and dried in the 60° oven, giving 3.8 g. Recrystallization from aqueous ethanol gave white needles, unmelted aboove 300°.

Anal Calcd. for $C_{11}H_8N_3Cl$: C, 60.70; H, 3.70; N, 19.31; Cl, 16.29. Found: C, 60.68; H, 4.01; N, 18.79; Cl, 16.30

D. 9-Anilino-7-methyl-1H-imidazo[4,5-f]quinoline Hydrochloride

A mixture of 11 g. (0.05 mole) of C. and 5 g. (0.05 mole) of aniline in 600 ml. of ethanol was refluxed for 6 hr. The solvent was removed in vacuo and the residue was slurried with ether. The crude product was collected by filtration as tan needles and was recrystallized from ethanol. The product was collected as tan needles melting at 350°–355° in a yield of 6.2 g. (40%). Recrystallization from ethanol raised the melting point to 368°–370° (corr.).

Anal. Calcd. for $C_{17}H_{14}N_4.HCl$: C, 65.38; H, 5.00; N, 17.80. Found: C, 65.35; H, 4.99;N, 17.71.

Example II

9-(β-Naphthylamino)-7-methyl-1H-imidazo[4,5-f]-quinoline Hydrochloride

A mixture of 27 g. (0.124 m.) of the compound of Example I, C. and 17.8 g. (0.124 m.) of β-naphthylamine in 200 ml. of ethanol was stirred and refluxed overnight. The reaction solution was concentrated in vacuo to give 43 g. m.p. 377°–380° with decomposition. After dissolving the crude product in 3000 ml. of MeOH, with charcoal, the filtrate was concentrated to a volume of 500 ml. then chilled. The yield after oven-drying (100°) was 30 g., m.p. 384°–386°.

Anal. Calcd. for $C_{21}H_{16}N_4.HCl$: C, 69.90; H, 4.75; N, 15.53 Cl 9.83. Found: C, 69.56; H, 4.68; N, 15.44; Cl, 10.03.

Example III

9-Methylanilino)-7-methyl-1H-imidazo[4,5-f]quinoline Hydrochloride

A mixture of 30 g. (0.138 m.) of the compound of Example I, C., 14.81 g. (0.138 m.) of p-toluidine and 600 ml. of ethanol was refluxed with stirring overnight. The reaction mixture was concentrated to dryness in vacuo, and the residue dissolved in 3000 ml. of ethanol. The insolubles were removed by filtration and the ethanol filtrate concentrated in vacuo to give 21 g. m.p. 388°–390°. The crude product was recrystallized from 500 ml. of dimethylformamide to yield 15 g. m.p. > 400°.

Anal. Calcd. for $C_{18}H_{16}N_4.HCl$: C, 66.56: H, 5.28; N, 17.25; Cl, 10.92. Found: C, 66.40; H, 5.14; N, 17.31; Cl, 10.91.

Example IV 9-(2-Chloro-5-methylanilino)-7-methyl-1H-imidazo[4,5-f]quinoline Hydrochloride A mixture of 40 g. (0.184 m.) of the compound of Example I, C., 26.1 g. (0.184 m.) of 2-chloro-5-methylaniline and 500 ml. of ethanol was refluxed with stirring overnight. The reaction mixture was concentrated to dryness in vacuo, and the residue dissolved in 700 m. of MeOH. The insolubles were removed by filtration and the MeOh filtrate concentrated in vacuo to give 24 g. m.p. decomposes 315°–400°C. The crude product was triturated in 500 ml. of MeOH, then oven-dried (100°C) to give m.p. 332°–335°C.

Anal. Calcd. for $C_{18}H_{15}ClN_4.HCl$: C, 60.17; H, 4.49; N, 15.60; Cl, 19.74. Found: C, 59.79; H, 4.36; N, 15.53; Cl, 19.61.

Example V 9-(p-n-Butylanilino-7-methyl-1H-imidazo[4,5-f]quinoline Hydrochloride A mixture of the compound of Example I, C. (21.7 g., 0.1 mole) and p-n-butylaniline (14.9 g., 0.1 mole) in ethanol (200 ml.) was stirred and refluxed overnight. The reaction solution was concentrated to dryness by rotary evaporator and the residue was collected and dried at 100°C to yield 36.5 g. (99.7%) yellow crystals, m.p. 296°–303°C. A small sample (5.0 g.) was recrystallized from nitromethane (750 ml.) and dried to yield 1.9 g. yellow crystals, m.p. 287°–302°C. A repeated recrystallization gave m.p. 303°–306°C.

Anal. Calcd. for $C_{21}H_{22}N_4.HCl$: C, 68.74; H, 6.32; N, 15.27. Found: C, 68.50; H, 6.26; N, 15.36.

Example VI 9-(3Chloro-4-methylanilino)-7-methyl-1H-imidazo[4,5-f]quinoline Hydrochloride A 500 ml., 3-neck, r.b. flask fitted with stirrer, condenser, and thermometer was charged with a mixture of the compound of Example I, C. (21.7 g., 0.1 mole), 3-chloro-4-methylaniline (14.2 g., 0.1 mole) and ethanol (300 ml.). The mixture was heated at reflux, while stirring, overnight. The near solution was concentrated to dryness by rotary evaporator and the residue was collected and dried to yield 35 g. (97.5%), m.p. 352°–364°C (dec). A 10 g. sample was dissolved in methanol (200 ml.), treated with charcoal and filtered while hot. Ether (ca 750 ml.) was added until the filtrate remained turbid and was then chilled. The crystals were collected by filtration and dried to yield 3.4 g. yellow crystals, m.p. 362°–370°C (dec). After two recrystallizations a m.p. 368°–372°C (dec) was obtained.

Anal. Calcd. for $C_{18}H_{15}ClN_4.HCl$: C, 60.17; H, 4.49; N, 15.60. Found: C, 59.76; H, 4.43; N, 15.30.

Example VII

7-Methyl-9-(3-trifluoromethylanilino)-1H-imidazo[4,5-f]quinoline Hydrochloride

A mixture of 16 g. (0.1 m.) of m-trifluoromethylaniline, 22 g. of the compound of Example I, C. and 200 ml. of dimethylformamide was heated overnight on the steam bath, then heated under reflux for 1½ hours and allowed to cool. the crystalline product was filtered, washed with a little dimethylformamide, air-dried briefly and recrystallized from 350 ml. of ethanol to give 25 g. as white needles, m.p. 300°–307°.

Anal. Calcd. for $C_{18}H_{13}F_3N_4.HCl.½H_2O$: C, 55.75; H, 3.90; N, 14.45. Found: C, 55.69; H, 4.10; N, 14.39.

Example VIII 9-(α-Naphthylamino)-7-methyl-1H-imidazo[4,5-f]quinoline Hydrochloride Tetartohydrate A 500 ml., 3-neck, r.b. flask fitted with stirrer, condenser and thermometer was charged with the compound of Example I, C. (16.3 g., 0.075 mole), α-naphthylamine (10.7 g., 0.076 mole) and dimethylformamide (300 ml). The mixture was stirred overnight while heating at reflux. The reaction mixture was then concentrated to dryness by rotary evaporator. The residue was collected by filtration, washed with ether and dried at 60° to yield 20.5 g. (76%) yellowish crystals, m.p. 351°–357°. The product was dissolved in methanol (2000 ml.), was treated with charcoal, filtered while hot and left standing overnight. The crystals were collected by filtration and dried at 100°C to yield 11.3 g. yellow crystals m.p. 355°–361°C. The filtrate was concentrated to 900 ml. by rotary evaporator and chilled. The crystals were collected by filtration and dried to yield 3.9 g. light yellow crystals, m.p. 351°–355°C. The two crops were combined.

Anal. Calcd. for $C_{21}H_{18}N_4.HCl.¼H_2O$: C, 69.03; H, 4.63; N, 15.34. Found: C, 68.63; H, 4.75; N, 15.27.

Example IX 9-(p-sec-Butylanilino)-7-methyl-1H-imidazo[4,5-f]quinoline Hydrochloride Tetartohydrate A. Preparation of p-sec-butylaniline:

A 500 ml. reduction bottle charged with a mixture of p-nitro-sec-butylbenzene (17.9 g., 0.1 mole) and ethanol (200 ml.) was shaken with hydrogen over ½ teaspoon Raney active nickel catalyst in water. A hydrogen uptake of 25 psi was recorded (calcd. 25.9 psi). The catalyst was removed by filtration and the filtrate was used in part B.

B. Preparation of title compound:

A 500 ml. 3-neck, r.b. flask fitted with stirrer, condenser and thermometer was charged with the filtrate from part A plus the compound of Example I, C. (21.7 g. 0.1 mole) and was stirred overnight while heating at reflux. The reaction mixture was concentrated to dryness by rotary evaporator. The residue was collected and dried to yield 36 g. (98%) yellow crystals, softens 75°–80°C, melts 210°–225°C. The crude product was dissolved in methanol (400 ml.), treated with charcoal and filtered while hot. The filtrate was diluted with ether (3000 ml.) with scratching and chilled. The crystals were collected by filtration and dried to yield 22.1 g. yellow crystals, m.p. 234°C.

Anal. Calcd. for $C_{21}H_{22}N_4 \cdot HCl \cdot \frac{1}{4}H_2O$: C, 67.91; H, 6.38; N, 15.09. Found: C, 67.67; H, 6.51; N, 15.14.

Example X

9-[4-Chloro-3-(trifluoromethyl)anilino]-7-methyl-1H-imidazo[4,5-f]quinoline Hydrochloride Hydrate A stirred mixture of the compound of Example I, C. (22 g. 0.1 mole) and 5-amino-2-chlorobenzotrifluoride (20 g. 0.1 mole) in 200 ml. of dimethylformamide, was refluxed for 6 hours. The reaction solution was stripped in vacuo to give 35 g. (82%) of tan product.

Anal. Calcd. for $C_{18}H_{12}ClF_3N_2 \cdot HCl \cdot 3/4H_2O$: C, 50.66; H, 3.42; N, 13.13 Found: C, 51.04; H, 3.69; N, 12.84.

Example XI 9-(o-Phenylanilino)-7-methyl-1H-imidazo[4,5-f]quinoline Hydrochloride Tetartohydrate A stirred mixture of the compound of Example I, C. (22 g., 0.1 mole) and 2-aminobiphenyl (17 g. 0.1 mole) in 200 ml. of dimethylformamide was refluxed for 6 hours. The reaction solution was stripped in vacuo to yield a semisolid. The semisolid was recrystallized from methanol/ether to give 23 g. (59%) of tan product, m.p. 270°–272°C.

Anal. Calcd. for $C_{23}H_{18}N_4 \cdot HCl \cdot \frac{1}{4}H_2O$: C, 70.58; H, 5.02; N, 14.32. Found C, 70.66; H, 4.87; N, 14.53.

Example XII 9-(3-Chloro-2-methylanilino)-7-methyl-1H-imidazo[4,5-f]quinoline Hydrochloride Monohydrate A stirred reaction mixture of the compound of Example I, C. (22 g., 0.1 mole) and 3-chloro-2-methylaniline (14 g., 0.1 mole) in 200 ml. of dimethylformamide was refluxed for 6 hours. The reaction mixture was stripped in vacuo to yield a tar. Upon standing the tar solidified to give a yellow semisolid. The yellow product was recrystallized twice from methanol/ether to yield 14 g. (37%).

Anal. Calcd. for $C_{18}H_{15}ClN_4 \cdot HCl \cdot H_2O$: C, 58.30; H, 4.81; N, 14.85 Found: C, 56.98; H, 4.69; N, 14.69.

Example XIII 9-(p-Isopropylanilino)-7-methyl-1H-imidazo[4,5-f]quinoline Hydrochloride Hemihydrate A mixture of the compound of Example I, C. (32.1 g., 0.148 mole), p-isopropylaniline (20 g., 0.148 mole) and ethanol (300 ml.) was stirred while heating at reflux for 4 hours. The mixture was chilled and the crystals were collected by filtration and dried at 60°C to yield 3.6 g. off-white crystals, m.p. 215°–230°C. The filtrate was concentrated to 150 ml. by rotary evaporator and chilled. The solid was collected and dried to yield 29.7 g. off white crystals, m.p. 249°–256°C. A third crop was collected and dried to yield 7.1 g. off white crystals, m.p. 249°–256°C. Crop I was dissolved in isopropanol (900 ml.), treated with charcoal and filtered while hot. The filtrate was concentrated to 50 ml. The grayish mixture was chilled for several hours and the crystals were collected and dried to yield 0.1 g. gray crystals, m.p. 224°–232°C - discarded. A second crop was collected and dried to yield 0.3 g. yellow crystals, m.p. 248°–254°C.

Anal. Calcd. for $C_{20}H_{20}N_4 \cdot HCl \cdot \frac{1}{2}H_2O$: C, 66.38; H, 6.13; N, 15.48. Found: C, 66.71; H, 6.08; N, 15.45.

Example XIV 9-(3,4-Dichloroanilino)-7-methyl-1H-imidazo[4,5-f]quinoline Hydrochloride Hemihydrate A solution of the compound of Example I, C. (22 g., 0.1 mole) and 3,4-dichloroaniline (16.2 g., 0.1 mole) in ethyl alcohol (1200 ml.) was refluxed for six hours. At the end of this period the solution was filtered and the solvent reduced in volume by evaporation. Addition of ether to the concentrated solution precipitated a crystalline product which was isolated and dried at 60° to give 19 g. of crude compound. This was combined with 44 g. from another run and recrystallized twice from ethyl alcohol, combined with 23 g. from a third run and recrystallized from methanol to give 33 g. (17%).

Anal. Calcd. for $C_{17}H_{12}Cl_2N_4 \cdot HCl \cdot \frac{1}{2}H_2O$: C, 52.63; H, 3.63; N, 14.42. Found: C, 52.35; H, 3.85; N, 14.39.

Example XV 9-(p-Bromoanilino)-7-methyl-1H-imidazo[4,5-f]quinoline Hydrochloride A mixture of 37.9 g. (0.174 m.) of the compound of Example I, C., 30 g. (0.174 ml.) of p-bromoaniline and 500 ml. of ethanol was stirred and refluxed overnight. After concentrating in vacuo the residue was recrystallized from 500 m. of MeOH to give 55 g. m.p. 347°–349°.

Anal. Calcd. for $C_{17}H_{13}BrN_4 \cdot HCl$: C, 52.39; H, 3.62; N, 14.38; Cl, 9.10. Found C, 52.07; H, 3.75; N, 14.25; Cl, 9.01.

Example XVI 9-(4-Iodoanilino)-7-methyl-1H-imidazo[4,5-f]quinoline Hydrochloride A 500 ml., 3-neck, r.b. flask fitted with stirrer, condenser and thermometer was charged with the compound of Example I, C. (24.8 g., 0.114 mole), 4-iodoaniline (25 g., 0.114 mole) and ethanol (300 ml.). The mixture was stirred and heated overnight. The mixture was concentrated to dryness by rotary evaporator and the residue was collected and dried at 100°C to yield 49 g. (97.7%) brown crystals, m.p. 296°–305°C. Recrystallization from ethanol gave m.p. 313°–315°C.

Anal. Calcd. for $C_{17}H_{13}IN_4 \cdot HCl$: C, 46.76; H, 3.23; N, 12.83. Found: C, 46.45; H, 3.38; N, 12.62.

Example XVII 9-(p-Dimethylaminoanilino)-7-methyl-1H-imidazo[4,5-f]quinoline Hydrochloride Sesquihydrate A mixture of 33 g. (0.15 mole) of the compound of Example I, C. and 21 g. (0.15 mole) of p-dimethylaminoaniline in 1800 ml. of ethanol was refluxed overnight. The solvent was removed by evaporation in vacuo. The residue was recrystallized from ethanol to give 32 g. of yellow solid. The solid was dissolved methyl alcohol and was acidified with a saturated etherhydrogen chloride solution. The product was collected as a cream colored solid and was recrystallized from methyl alcohol to give a yellow solid melting at 210°–215° in a yield of 22 g. (42%). Recrystallization from methyl alcohol raised the melting point to 215°–217°.

Anal. Calcd. for $C_{19}H_{19}N_5 \cdot HCl \cdot \frac{1}{2}H_2O$: C, 59.91; H, 6.09; N, 18.39. Found: C, 60.29; H, 5.93; N, 18.37.

EXAMPLE XVIII 9-(p-Diethylamino-anilino)-7-methyl-1H-imidazo[4,5-f]quinoline Hydrochloride A mixture of 26.4 g. (0.122 m.) of the compound of Example I, C. 20 g. (0.122 m.) of N,N-diethyl-p-phenylenediamine and 200 ml. of ethanol was stirred and heated at reflux overnight. The solution was concentrated in vacuo to give 43 g. m.p. 293°–295°. The crude product was recrystallized from 500 ml. of MeOH and precipitated with the addition of 500 ml. of ether. The yield after oven-drying (100°) was 33 g. m.p. 297°–299°.

Anal. Calcd. for $C_{21}H_{23}N_5 \cdot HCl$: C, 66.04; H, 6.33; N, 18.34; Cl, 9.28. Found: C, 66.08; H, 6.34; N, 18.34; Cl, 9.17.

EXAMPLE XIX

9-[3,Chloro-4-(dimethylamino)anilino]-7-methyl-1H-imidazo[4,5-f]quinoline Hydrochloride A. 2-Chloro-N,N-dimethyl-4-nitroaniline A solution of 52 g. (0.27 m.) of 1,2-dichloro-4-nitrobenzene, 122 g. (1.08 m.) of 40% methylamine in $H_2O$ and 300 ml. of ethanol was refluxed overnight. After chilling, the bright yellow precipitate was collected by filtration and airdried to give 52 g. m.p. 71°–73°.

B. 9-[3-Chloro-4-(dimethylamino)anilino]-7-methyl-1H-imidazo[4,5-f]qunioline Hydrochloride A mixture of 52 g. (0.25 m.) of 2-chloro-N,N-dimethyl-4-nitroaniline (part A) and 500 ml. of ethanol was subjected to hydrogenation over one teaspoon of Raney active nickel catalyst in water. The hydrogen uptake was 53 psi. (calcd. 52.2 psi.). The catalyst was removed by filtration and 56.5 g. (0.26 m.) of the compound of Example I, C. added to the ethanol filtrate. The reaction solution was stirred and refluxed overnight and then concentrated to dryness in vacuo. The residue was recrystallized from 1000 ml. of ethanol, then concentrated to a volume of 300 ml. A second recrystallization from 1000 ml. of ethanol gave 25 g. m.p. 338°–340°.

Anal. Calcd. for $C_{19}H_{18}ClN_5 \cdot HCl$: C, 58.77; H, 4.93; N, 18.04; Cl, 18.26. Found: C, 58.80; H, 4.97; N, 18.01; Cl, 17.48.

EXAMPLE XX 9-(4-Piperidinonanilino)-7-methyl-1H-imidazo[4,5-f]quinoline Hydrochloride A. Preparation of 1-Piperidino-4-nitrobenzene:

A 500 ml., 3-neck, r.b. flask fitted with stirrer, condenser and thermometer was charged with p-nitrochlorobenzene (40 g., 0.255 mole) and piperidine (42.5 g., 49.4 ml., 0.5 mole). The mixture was heated, with stirring, at steam bath temperature for 2½ hr. At the end of this time, the reaction mixture was diluted with water (100 ml.) and stirred thoroughly. The precipitate was removed by filtration - after cooling to about 30°C and recrystallized from ethanol (300 ml.) and filtered while hot. The filtrate was chilled and the crystals were collected by filtration and dried at 60°C to yield 35.7 g (67.8%) gold crystals, m.p. 96°–99°C.

B. Preparation of title compound:

1. The 1-piperidino-4-nitrobenzene (35.7 g., 0.173 mole) was placed in a 500 ml. reduction bottle with ethanol (200 ml.). The compound was reduced with hydrogen over one-half teaspoon of Raney active nickel catalyst in water. A hydrogen uptake of 40 psi was recorded (calcd. 51.6 psi). The catalyst was removed by filtration.

2. A 500 ml., 3-neck, r.b. flask fitted with condenser, stirrer and thermometer was charged with the compound of Example I, C. (37.5 g., 0.173 mole). The above filtrate (1) was added to the compound of Example I, C. and the mixture was stirred and refluxed overnight. The reaction mixture was concentrated to dryness by rotary evaporator and the residue was collected and dried to yield 68.5 g. (101%) greenish-yellow crystals, m.p. 328°–338°C. A portion (10 g.) of the crude material was dissolved in anhydrous methanol (100 ml.), treated with charcoal and filtered while hot. The filtrate was concentrated to about 20 ml. and chilled. The crystals were collected by filtration and dried at 100°C to yield 1.3 g. yellow crystals, m.p. 338°–350°C.

Anal. Calcd. for $C_{22}H_{23}N_5 \cdot HCl$: C, 67.08; H, 6.14; N, 17.78. Found: C, 66.72; H, 6.15; N, 17.64.

Example XXI

9-[4-(4-Methylpiperazino)anilino]-7-methyl-1H-imidazo[4,5-f]quinoline Hydrochloride Hydrate A. Preparation of 4-(4-Methylpiperazino)nitrobenzene:

A 500 ml. 3-neck, r.b. flask fitted with stirrer, condenser and thermometer was charged with p-nitrochlorobenzene (39.3 g., 0.25 mole) and N-methylpiperazine (50 g., 0.5 mole) and heated at about 130°, while stirring, for 4 hours. The reaction mixture was ground in a mortar with about 300 ml. of water. The solid was removed by filtration, washed with water and the product was then recrystallized from ethanol (80 ml.), treated with charcoal, filtered while hot and chilled. The crystals were collected by filtration and dried at 60°C to yield 35.2 g. (63.7%) reddish-yellow crystals, m.p. 98°–101°C.

B. Preparation of title compound:

1. The 4-(4-methylpiperazino)nitrobenzene (35.2 g., 0.159 mole) and ethanol (200 ml.) were placed in a 500 ml. reduction bottle. The compound was reduced with hydrogen over one-half teaspoon of Raney active nickel catalyst in water. A hydrogen uptake of 41 psi was recorded (calcd. 42.3 psi). The catalyst was removed by filtration.

2. A 500 ml., 3-neck, r.b. flask fitted with stirrer, condenser and thermometer was charged with the compound of Example I, C. (34.5 g. 0.159 mole). The above filtrate (1) was added to the compound of Example I, C. and the mixture was stirred and refluxed overnight. The reaction mixture was concentrated to dryness by rotary evaporator and the residue was collected and dried at 100°C to yield 64.6 g. (92,3%) green crystals, m.p. 296°–314° (dec.). The crude product (54 g.) was dissolved in anhydrous methanol (ca. 1500 ml.), treated with charcoal and filtered while hot. Ether (ca. 1500 ml.) was added until the filtrate became turbid and the mixture was chilled. The crystals were collected by filtration and dried at 100°C to yield 24.5 g. green crystals, m.p. 317°–319° (dec.).

Anal. Calcd. for $C_{22}H_{24}N_6 \cdot HCl \cdot 1\frac{3}{4}H_2O$: C, 59.99; H, 6.52; N, 19.08. Found: C, 60.06; H, 6.42; N, 18.87.

Example XXII

9-(M-Dimethylamino)anilino)-7-methyl-1H-imidazo[4,5-f]quinoline Hydrochloride A. Preparation of N,N-Dimethyl-m-phenylenediamine:

N,N-Dimethyl-m-nitroaniline (25 g., 0.15 mole) was placed in a 500 ml. reduction bottle with ethanol (200 ml.). The mixture was shaken with hydrogen over ½ teaspoon of Raney active nickel catalyst in water. A hydrogen uptake of 45 psi was recorded (calcd. 38.8 psi). The catalyst was removed by filtration and the filtrate was concentrated to dryness by rotary evaporator. The product, which is a deep reddish oily liquid, was identified by I.R.

B. Preparation of title compound:

A 500 ml., 3-neck, r.b. flask fitted with stirrer, condenser and thermometer was charged with the compound of Example I, C. (30.4 g., 0.14 mole), N,N-dimethyl-m-phenylenediamine (19 g., 0.14 mole) and ethanol (300 ml.) and the whole was heated at reflux while stirring overnight. The reaction mixture was concentrated to dryness by rotary evaporator. The residue was collected and dried to yield 50.6 g. (102%) yellow-brown crystals, m.p. 304°–311°C (dec.). Recrystallization from methanol gave m.p. 313°–317°C.

Anal. Calcd. for $C_{19}H_{19}N_5 \cdot HCl$: C, 64.49; H, 5.70; N, 19.79. Found: C, 64.65; H, 5.59; N, 19.66.

Example XXIII

9-(3-Chloro-4-piperidinoanilino)-7-methyl-1H-imidazo[4,5-f]quinoline Hydrochloride Tetartohydrate A. Preparation of 2-chloro-1-piperidino-4-nitrobenzene:

A 250 ml., 3-neck, r.b. flask, fitted with stirrer, condenser and thermometer was charged with 1,2-dichloro-4-nitrobenzene (19.2 g., 0.1 mole) and piperidine (17 g., 19.8 ml., 0.2 mole). The mixture was stirred for 3½ hr. while heating at 95°C. The reaction mixture was then diluted with water (ca. 300 ml.) and stirring continued as the mixture cooled. The solid was collected by filtration and recrystallized from ethanol (70 ml.) to yield 15.8 g. (65.8%) yellow crystals, m.p. 36°–41°C.

Anal. Calcd. for $C_{11}H_{13}ClN_2O_2$: C, 54.89; H, 5.44; N, 11.64. Found : C, 55.14; H, 5.42; N, 11.48.

B. Preparation of 3-chloro-4-piperidinoaniline:

2-Chloro-1-piperidino-4-nitrobenzene (14.4 g., 0.06 mole) was placed in a 500 ml. reduction bottle with ethanol (200 ml.). The mixture was shaken with hydrogen over ½ teaspoon Raney active nickel catalyst in water. A hydrogen uptake of 14 psi was recorded (calcd. 15.5 psi). The catalyst was removed by filtration and the filtrate was concentrated to dryness by rotary evaporator. The 12 g. (95.3%) of oily liquid was identified by I.R.

C. Preparation of title compound:

A 500 ml. 3-neck, r.b. flask fitted with condenser, thermometer and stirrer was charged with the compound of Example I, C. (12.4 g 0.0572 mole), 3-chloro-4-piperidinoaniline (12 g. 0.0572 mole) and ethanol (300 ml.) and the mixture was stirred overnight while heating at reflux. The reaction solution was concentrated to dryness by rotary evaporator. The residue was collected and dried to yield 23.9 g. (97.9%) yellow crystals which soften 198°–205°C and melt 225°–240°C. The crude product (21.9 g.) was dissolved in methanol (250 ml.), treated with charcoal and filtered while hot. The filtrate was diluted with ether (ca. 150 ml.) until the filtrate remained turbid and was then chilled. The crystals were collected by filtration and dried to yield 12.3 g. yellow crystals m.p. 265°–273°C.

Anal. Calcd. for $C_{22}H_{22}ClN_5 \cdot HCL \cdot ¼H_2O$: C, 61.04; H, 5.47; N, 16.18. Found: C, 60.81; H, 5.29; N, 16.07.

Example XXIV

9-[3-Chloro-4-(N-methylpiperazinoanilino)]-7-methyl-1H-imidazo[4,5-f]-quinoline Dihydrochloride Hydrate A. Preparation of 2-chloro-1-(N-methylpiperazino)-4-nitrobenzene:

A 500 ml., 3-neck, r.b. flask fitted with stirrer, condenser, and thermometer was charged with 1,2-dichloro-4-nitrobenzene (48 g., 0.25 mole) and N-methylpiperazine (50 g. 0.5 mole) and the mixture was stirred for 3½ hour while heating at 130°–140°C. The reaction solution was cooled to about 100°C and diluted with water (ca. 400 ml.). The product was collected by filtration and recrystallized from ethanol (175 ml.) to yield 49.4 g. yellow crystals m.p. 99°–100°C. The filtrate was concentrated to 50 ml. by rotary evaporator and chilled. The crystals were collected and dried to yield 3.8 g. yellow crystals, m.p. 93°–96°C. Total yield 53.2 g. (85.2%)

B. Preparation of 4-(1-methylpiperazino)-3-chloroaniline:

2-Chloro-1-(N-methylpiperazino)-4-nitrobenzene (36.4 g., 0.143 mole) was placed in a 500 ml. reduction bottle with ethanol (200 ml.). The compound was shaken with hydrogen over ½ teaspoon of Raney active nickel catalyst in water. A hydrogen uptake of 33 psi was recorded (calcd. 36.98 psi). The catalyst was removed by filtration and the filtrate was concentrated to 70 ml. by rotary evaporator and chilled. The crystals were collected by filtration and dried at 60°C to yield 24.8 g. (77%) gray crystals, m.p. 123°–126°C.

C. Preparation of title compound:

A 1000 ml. 3-neck, r.b. flask fitted with stirrer, condenser, and thermometer was charged with the compound of Example I, C. (42.7 g. 0.197 mole), 4-(1-methylpiperazino)-3-chloroaniline (44.3 g 0.197 mole) and dimethylformamide (800 ml.). The mixture was stirred overnight while heating at 120–130°C. The reaction solution was concentrated to dryness by rotary evaporator. The residue was taken up in methanol (ca. 600 ml.) and filtered while hot. The filtrate was concentrated to 300 ml. by rotary evaporator and then slowly diluted with ether (1200 ml.) and chilled. The crystals were collected by filtration and dried at 100°C.

Anal. Calcd. for $C_{22}H_{23}ClN_6 \cdot 2HCL \cdot 3½H_2O$: C, 48.67; H, 5.94; N, 15.48. Found : C, 48.66; H, 5.67; N, 15.17.

Example XXV

9-(2-Piperidino-5-aminopyridine)-7-methyl-1H-imidazo[4,5-f]quinoline Hydrochloride Tetartohydrate A. Preparation of 2-piperidino-5-nitropyridine:

A 500 ml. 3-neck, r.b. flask fitted with stirrer, thermometer, condenser, and dropping funnel was charged with a mixture of 2-chloro-5-nitropyridine (23.7 g. 0.15 mole) in ethanol (100 ml.). To the mixture was added, dropwise with stirring, a solution of piperidine (25.5 g., 29.6 ml. 0.3 mole) in ethanol (200 ml.) and the mixture was heated at reflux, while stirring, for 3 hr. The solution was treated with charcoal and filtered while hot. The filtrate was chilled and the crystals were collected by filtration and dried at 60°C to yield 24.6 g. (79.4%) yellow crystals, softening 74°–79°C, melts 198°–205°C.

Anal. Calcd. for $C_{10}H_{13}N_3O_2$: C, 57.96; H, 6.32; N, 20.28. Found : C, 57.97; H, 6.24; N, 20.02.

B. Preparation of 2-piperidino-5-aminopyridine:

A mixture of 2-piperidino-5-nitropyridine (22.6 g. 0.109 mole) and ethanol (200 ml.) was shaken in a 500 ml. reduction bottle with hydrogen over ½ teaspoon Raney active nickel catalyst in water. A hydrogen uptake of 21 psi was recorded (calcd. 27.9 psi). The catalyst was removed by filtration and the filtrate was concentrated to dryness by rotary evaporator to yield 18 g. dark red syrup identified by I.R.

C. Preparation of title compound:

A 500 ml., 3-neck, r.b. flask fitted with stirrer, condenser and thermometer was charged with 2-piperidino-5-aminopyridine (18 g., 0.102 mole), the compound of Example I, C. (22.2 g., 0.102 mole) and ethanol (300 ml.). The mixture was heated at reflux overnight while stirring. The reaction mixture was cooled to room temperature and ether (200 ml.) was added and the mixture was chilled in an ice bath. The dark green mixture was added and the mixture was chilled in an ice bath. The dark green mixture was filtered and the crystals dried to yield 14.1 g. (35%), m.p. 358°–368°C.

Anal. Calcd. for $C_{21}H_{22}N_6.HCl.\frac{1}{2}H_2O$: C, 63.15; H, 5.93; N, 21.04. Found : C, 63.20; H, 5.85; N, 20.85.

Example XXVI

9-[4-(4-Benzylpiperazino)-3-chloroanilino]-7-methyl-1H-imidazo[4,5-f]-quinoline Hydrochloride A. Preparation of 1-(1-benzylpiperazino)-2-chloro-4-nitrobenzene:

A 500 ml. 3-neck, r.b. flask fitted with stirrer, condenser and thermometer was charged with 1,2-dichloro-4-nitrobenzene (19.2 g., 0.1 mole), 1-benzylpiperazine (35.2 g., 0.2 mole) and dimethylformamide (200 ml.) and the mixture was stirred for 2-1/1 hour while heating at reflux. The reaction solution was transferred to a 2000 ml. separatory funnel containing water (500 ml.) and shaken thoroughly. The mixture was then extracted with ether (500 ml.). The organic layer was separated and dried over magnesium sulfate overnight. The salt was removed by filtration and the filtrate was concentrated to dryness by rotary evaporator. The residue was dissolved in ethanol (125 ml.) and filtered while hot. The filtrate was chilled and the crystals collected by filtration and dried at 60°C to yield 22.5 g. yellow crystals, m.p. 92°–95°C. An additional recrystallization gave a sample m.p. 93°–95°C.

Anal. Calcd. for $C_{17}H_{18}ClN_3O_2$: C, 61.54; H, 5.47; N, 12.67. Found : C, 61.54; H, 5.34; N, 12.79.

B. Preparation of 4-(4-benzylpiperazino)-3-chloroaniline:

A 500 ml. reduction bottle was charged with a mixture of 1-(1-benzylpiperazino)-2-chloro-4-nitrobenzene (22.5 g. 0.068 mole) and dimethylformamide (200 ml.). The mixture was shaken with hydrogen over ½ teaspoon Raney active nickel catalyst in water. A hydrogen uptake of 16 psi was recorded (calcd. 17.6 psi). The catalyst was removed by filtration and the filtrate used in part C.

C. Preparation of title compound:

A 500 ml., 3-neck, r.b. flask fitted with stirrer, condenser and thermometer was charged with the filtrate from part B, the compound of Example I, C. (14.8 g., 0.068 mole) plus an additional 100 ml. dimethylformamide. The mixture was stirred overnight while heating at reflux. The solution was chilled and the crystals were collected by filtration and dried at 100°C to yield 21.4 g. (50.6%), m.p. 216°–226°C.

Anal. Calcd. for $C_{28}H_{27}ClN_6.HCL$: C, 64.74; H, 5.43; N, 16.18. Found : C, 64.47; H, 5.46; N, 16.16.

Example XXVII

7-Methyl-9[6-(4-methyl-1-piperazinyl)-3-pyridyl]amino)-1H-imidazo[4,5-f]quinoline Hydrochloride Hydrate A. Preparation of 2-(N-methylpiperazino)-5-nitropyridine A 500 ml. 3-neck, r.b. flask fitted with y-tube and condenser and thermometer, stirrer and addition funnel was charged with a mixture of 2-chloro-5-nitropyridine (15.8 g. 0.1 mole) in ethanol (300 ml.). To this was added N-methylpiperazine (20 g. 0.2 mole) dropwise while stirring. After the addition (ca. 5 min.), the mixture was heated at reflux for 3 hr. while stirring continued. The solution was chilled to 5°C and the crystals were collected by filtration and dried at 60°C to yield 12 g. yellow crystals, m.p. 94°–96°C.

Anal. Calcd. For $C_{10}H_{14}N_4O_2$: C, 54.04; H, 6.35; N, 25.21. Found : C, 53.83; H, 6.17, N, 25.15.

B. Preparation of 2-(N-methylpiperazino)-5-aminopyridine:

A 500 ml. reduction bottle was charged with 2-(N-methylpiperazino)-5-nitropyridine (13.5 g., 0.0695 mole) and ethanol (200 ml.). The mixture was shaken with hydrogen over ½ teaspoon Raney active nickel catalyst in water. A hydrogen uptake of 14 psi was recorded (calcd. 18 psi). The catalyst was removed by filtration and the filtrate was used in part C.

C. Preparation of title compound:

A 1000 ml. flask fitted with stirrer, condenser and thermometer was charged with the filtrate from part B. To this was added the compound of Example 1, C. (20.1 g. 0.0927 mole) and an additional 400 ml. ethanol plus 215 ml. ethanolic HCl. The mixture was stirred overnight while heating at reflux. The mixture was chilled and the crystals were collected by filtration and dried at 60°C. to yield 24.7 g. m. p. 244°–250°C. The product was dissolved in methanol (300 ml.), treated with charcoal and filtered while hot. The filtrate was chilled and the crystals were collected and dried at 100°C. to yield 6.2 g. green crystals, m.p. 242°–262°C.

Anal. Calcd. for $C_{21}H_{23}N_7.2\frac{1}{2}HCl.H_2O$: C, 52.26; H, 5.74; N, 20.32; Cl, 18.37; $H_2O$, 3.73. Found : C, 52.46; H, 5.84; N, 20.39; Cl, 18.55; 18.41; $H_2O$, 3.81.

Example XXVIII 9-p-Anisidino-7-methyl-1H(or 3H)-imidazo[4,5-f]quinoline Hydrochloride A solution of 2.17 g. (0.01 m) of the compound of Example I, C. and 1.23 g.(0.01 m) of p-anisidine in 100 ml. of ethanol was heated under reflux for 6 hr. and then concentrated in vacuo to a sticky, clear residue. Addition of ether and scratching caused a yellow solid to separate. This was filtered, washed with ether and air-dried to give 2.55 g., m.p. ca. 175°–200°.

Anal. Calcd. for $C_{18}H_{16}N_4O.HCl.\frac{1}{2}H_2O$: C, 61.80; H, 5.19; Cl, 10.15. Found: C, 61.81; H, 5.36; Cl, 10.03.

Example XXIX
9-(p-Phenetidino)-7-methyl-1H-imidazo[4,5-f]quinoline Hydrochloride A mixture of 33 g. (0.15 mole) of the compound of Example I, C. and 23 g. (0.15 mole) of p-phenetidine in 1800 ml. of ethanol was refluxed for 6 hr. The solvent was removed by evaporation in vacuo and the residue was slurried with ether. The crude solid was collected by filtration and was recrystallized from ethanol. The product was collected as yellow needles melting at 229°–230° in a yield of 19 g. (36%). Recrystallization from ethanol raised the melting point to 330°–331°.

Anal. Calcd. for $C_{19}H_{18}N_4O \cdot HCl$: C, 64.31; H, 5.40; N, 15.79. Found: C, 64.11; H, 5.47; N, 15.64.

Example XXX
9(o-Anisidino)-7-methyl-1H-imidazo[4,5-f]quinoline Hydrochloride A mixture of 30 g. (0.138 m.) of the compound of Example I, C. 17 g. (15.6 ml. 0.138 m.) of o-anisidine and 200 ml. of ethanol was stirred and heated at reflux overnight. The solution was concentrated in vacuo to give 45 g. m.p. 271°–275°. The crude product was recrystallized from 350 ml. of MeOH. The yield after oven-drying (100°) was 29 g. m.p. 300°–301°.

Anal. Calcd. for $C_{18}H_{16}N_4O \cdot HCl$: C, 63.43; H, 5.03; N, 16.44; Cl, 10.40. Found: C, 63.47; H, 4.98; N, 16.34; Cl, 10.33.

Example XXXI
9-(3-Chloro-4-ethoxyanilino)-7-methyl-1H-imidazo[4,5-f]quinoline Hydrochloride A mixture of 20 g. (0.100 m.) of 3-chloro-4-ethoxynitrobenzene and 200 ml. of ethanol was subjected to hydrogenation over one-half teaspoon of Raney active nickel catalyst in water. A hydrogen uptake of 25 psi. was recorded (calcd. 25.8 psi.). The catalyst was removed by filtration and the filtrate stirred and refluxed overnight with 21.7 g. (0.100 m.) of the compound of Example I, C. The solution was concentrated in vacuo to give 36 g. m.p. 300°–307° with decomposition. After recrystallization from 300 ml. of MeOH, a yield of 23 g. m.p. 306°–309° with decomposition, was obtained.

Anal. Calcd. for $C_{19}H_{17}ClN_4O \cdot HCl$: C, 58.62; H, 4.66; N, 14.39; Cl, 18.22. Found: C, 58.80; H, 4.56; N, 14.59; Cl 17.82, 17.82.

Example XXXII
9-(p-Butoxyanilino)-7-methyl-1H-imidazo[4,5-f]quinoline Hydrochloride A. p-(n-Butoxy)nitrobenzene To a solution of p-nitrophenol (56.0 g. 0.4 mole) in acetone (400 ml.) was added n-butyl bromide (60.0 g., 0.44 mole) and potassium carbonate (anhydrous, 56.0 g., 0.4 mole). The mixture was heated on the steam bath for 48.0 hours. The acetone was removed from the reaction mixture in vacuo. Then, water (400 ml.) was added to the residue, which was extracted twice with benzene (200 ml. portions). The benzene layers were washed thrice with 10% sodium hydroxide solution (150 ml. portions). The washed layers of benzene were then dried over anhydrous potassium carbonate and the solvent was removed in vacuo. The product obtained after evaporation of the solvent was a crude yellow liquid (63.0 g. 79%). This was used in Part B without further purification.

B. 9-(p-Butoxyanilino)-7-methyl-1H-imidazo[4,5-f]quinoline hydrochloride

A mixture of 49 g. (0.25 m.) of p-butoxynitrobenzene and 600 ml. of ethanol was reduced with hydrogen over one teaspoon of Raney active nickel catalyst in water. A hydrogen uptake of 49 psi. was recorded (calcd. 50.5 psi). The catalyst was removed by filtration and the filtrate refluxed overnight with 54.5 g.(0.25 m.) of the compound of Example I, C. The solution was concentrated in vacuo to give 88 g. m.p. 284°–300° with decomposition. Recrystallization of ethanol, with charcoal and concentration of the filtrate gave 64 g. m.p. 317°–318°.

Anal. Calcd. for $C_{21}H_{22}N_4O \cdot HCl$: C, 65.87; H, 5.05; N, 14.64; Cl, 9.26. Found: C, 65.59; H, 6.07; N, 14.51; Cl, 9.23.

Example XXXIII
9-(m-Anisidino)-7-methyl-1H-imidazo[4,5-f]quinoline Hydrochloride A mixture of 40 g. (0.184m.) of the compound of Example I, C. 22.7 g.(20.7 ml., 0.184 m.) of m-anisidine and 500 ml. of ethanol was stirred and heated at reflux overnight. The solution was concentrated in vacuo to give 43 g. of crude product. It was then recrystallized from 2000 ml. of MeOH to give 35 g., m.p. 318°–322°C.

Anal. Calcd. for $C_{18}H_{16}N_4O \cdot HCl$: C, 63.43; H, 5.03; N, 16.44; Cl, 10.40. Found : C, 63.29; H, 5.07; N, 16.53; Cl, 10.39; 10.43.

Example XXXIV
9-(p-Phenoxyanilino)-7-methyl-1H-imidazo[4,5-f]quinoline Hydrochloride A mixture of 293 g. (0.135 m.) of the compound of Example I, C., 25 g. (0.135 m.) of p-phenoxyaniline and 500 ml. of ethanol was refluxed with stirring overnight. The reaction solution was chilled and the crude product collected by filtration, washed with ether and air-dried to give 47 g., m.p. 399°–341°C. It was then recrystallized from 2000 ml. of MeOH to yield 32 g., m.p. 342°–345°C.

Anal. Calcd. for $C_{23}H_{18}N_4O \cdot HCl$: C, 68.57; H, 4.75; N, 13.91; Cl, 8.80. Found : C, 68.17; H, 4.74; N, 13.86; Cl, 8.81.

EXAMPLE XXXV
9-(p-Methylmercaptoanilino)-7-methyl-1H-imidazo[4,5f]quinoline Hydrochloride Hydrate A mixture of 26.4 g. (0.12 m.) of the compound of Example 1, C., 16.7 g. (0.12 m.) of 4-methylmercaptoaniline and 500 ml. of ethanol was refluxed with stirring overnight. It was then concentrated in vacuo to give 50 g. m.p. 317°–320°C. The crude product was recrystallized from 500 ml. MeOH to yield 27 g., m.p. 318°–321°C.

Anal. Calcd. for $C_{18}H_{16}N_4S \cdot HCl \cdot H_2O$: C, 57,68: H, 5,11; N, 14.95; Cl, 9.46. Found : C, 58.03; H, 4.91; N, 15.13; Cl, 9.68; 9.79.

EXAMPLE XXXVI
9-(p-Benzyloxyanilino)-7-methyl-1H-imidazo[4,5-f]quinoline Hydrochloride Tetartohydrate A stirred mixture of the compound of Example I, C. (11 g. .05 mole), p-benzyloxyaniline hydrochloride (11.6 g. .0.5 mole), and triethylamine (5 g. .05 mole) in 200 ml. of ethanol was refluxed for 12 hours. The reaction solution was allowed to stand at room temperature for one day to give a precipitate. The solid was collected by filtration and discarded. The filtrate was stripped to dryness in vacuo to yield 21 g (100%) of product.

Anal. Calcd. for $C_{24}H_{19}N_4O.HCL.½H_2O$: C, 68.56; H, 4.91; N, 13.32. Found: C, 68.79; H, 4.94; N, 13.27.

EXAMPLE XXXVII 9-(2-Methylthioanilino)-7-methyl-1H-imidazo[4,5-f]quinoline Hydrochloride Hemihydrate A stirred mixture of the compound of Example I, C. (22 g. 0.1 mole) and 2-methylmercaptoaniline (14 g. 0.1 mole) in 200 ml. of dimethylformamide was refluxed for 4 hr. The reaction solution was left standing at room temperature overnight. A yellow precipitate was filtered to yield 40 g. (100%).

Anal. Calcd. for $C_{18}H_{16}N_4S.HCl.1/2\ H_2O$: C, 59.09; H, 4.96; N, 15.32. Found: C, 59.16; H, 4.85; N, 15.46.

EXAMPLE XXXVIII 9-(3-Methylthioanilino)-7-methyl-1H-imidazo[4,5-f]quinoline Hydrochloride A mixture of 21.7 g. (0.1 m.) of the compound of Example I, C., 13.9 g. (0.1 m.) of 3-methylmercaptoaniline and 250 ml. of dimethylformamide was refluxed overnight with stirring. It was chilled, filtered, washed with ether and air-dried to give 29 g. m.p. 310°–313°C.

Anal. Calcd. for $C_{18}H_{16}N_4S.HCl$: C, 60.59; H, 4.80; N, 15.70. Found: C, 60.38; H, 4.76; N, 15.57.

EXAMPLE XXXIX

9-[(6-Methoxy-3-pyridyl)amino]-7-methyl-1H-imidazo[4,5-f] quinoline

A stirred mixture of the compound of Example I, C. (22 g. 0.1 mole) and 5-amino-2-methoxypyridine (12 g., 0.1 mole) in 200 ml. of dimethylformamide, was refluxed for 6 hours. The reaction mixture, after standing at room temperature overnight, was filtered to give a tan solid. The solid was treated with dilute $NH_4OH$ and then filtered to yield 30 g. (98%) of tan product.

Anal. Calcd. for $C_{17}H_{15}N_5O$: C, 66.87; H, 4.95; N, 22.94. Found: C, 67.14; H, 4.91; N, 23.00.

EXAMPLE XL 9-(3,4-Dimethoxyanilino)-7-methyl-1H-imidazo[4,5-f] quinoline Hydrochloride A mixture of 20 g. (0.10 m.) of 4-nitroveratrole and 200 ml. of ethanol was reduced with hydrogen over one-half teaspoon of No. 28 Raney active nickel catalyst in water. A hydrogen uptake of 28.1 psi was observed (calcd. 28.5 psi). The catalyst was removed by filtration and the filtrate refluxed overnight with 23.7 g. (0.109 m.) of the compound of Example I, C. The solution was concentrated in vacuo to give 44g. m.p. 269°–274°. The product was recrystallized from 850 ml. of MeOH. The yield after overdrying (100°) was 25 g., m.p.271°–274°. Recrystallization from MeOH gave m.p. 278°–280°.

Anal. Calcd. for $C_{19}H_{18}N_4O_2.HCl$: C, 61.53; H, 5.16; N, 15.11; Cl, 9.56. Found: C, 60.99; H, 5.23; N, 14.97; Cl, 9.46.

EXAMPLE XLI 9-(3,4-Diethoxyanilino)-7-methyl-1H-imidazo[4,5-f quinoline Hydrochloride A mixture containing 40 g. (0.184 m.) of the compound of Example I, C., 33.4 g. (0.184 m.) of 3,4-diethoxyaniline and 500 ml. of ethanol was refluxed with stirring overnight. The mixture was chilled, and the crystalline solid collected by filtration, washed with ether and air-dried to give 72 g. m.p.278°–280°C.

Anal. Calcd. for $C_{21}H_{22}N_4O_2.HCl$: C, 63.23; H, 5.81; N, 14.25; CL, 8.89. Found : C, 62.79; H, 5.82; N, 13.99; Cl, 8.72.

EXAMPLE XLII 9-(3,4-Diisopropoxyanilino)-7-methyl-1H-imidazo[4,5-f]quinoline Hydrochloride A mixture of 25 g. (0.105 m) of 3,4-diisopropoxynitrobenzene and 200 ml. of ethanol was reduced with hydrogen over one-half teaspoon of Raney active nickel catalyst in water. A hydrogen uptake of 25 psi. was observed (calcd. 27 psi.). The catalyst was removed by filtration and the filtrate refluxed overnight with 22.7 g. (0.105 m.) of the compound of Example I, C. The solution was concentrated in vacuo to give 31 g. of yellow solid. The product was recrystallized from 150 ml. of ethanol and precipitated with ether to give 24.2 g., m.p. 279°–281°C.

Anal. Calcd. for $C_{23}H_{26}N_4O_2.HCl$: C, 64.70; H, 6.37; N, 13.13; Cl, 8.31. Found : C, 63.94; H, 6.60; N, 12.92; Cl, 8.13.

EXAMPLE XLIII 9-(3,4-Diisobutoxyanilino)-7-methyl-1H-imidazo[4,5-f]quinoline Hydrochloride A mixture of 26.3 g. (0.1 m.) of dimethallyloxynitrobenzene and 200 ml. of ethanol was shaken with hydrogen over one-half teaspoon of Raney active nickel catalyst in water. A pressure drop of 42 psi. was recorded (calcd. 43 psi.). The catalyst was removed by filtration and the ethanol filtrate refluxed overnight with21.7 g. (0.1 m.) of the compound of Example I, C. The solution was concentrated in vacuo and the product recrystallized from ethanol. The yield after oven-drying (100°C) was 22 g., m.p.273°–277°C.

Anal. Calcd. for $C_{25}H_{30}N_4O_2.HCl$: C, 65.59; H, 6.87; N, 12.32; Cl, 7.79. Found : C, 65.53; H, 6.74; N, 12.37; Cl, 7.79.

EXAMPLE XLIV 9-(3,4-Dibutoxyanilino)-7-methyl-1H-imidazo[4,5-f]quinoline Hydrochloride A mixture of 26.7 g. (0.1 m.) of 3,4-dibutoxynitrobenzene and 400 ml. of ethanol was shaken with hydrogen over one-half teaspoon of Raney active nickel catalyst in water. A pressure drop of 25.5 psi. was recorded (calcd. 25.8 psi.). The catalyst was removed by filtration and the filtrate refluxed overnight with 21.7 g. (0.1 m.) of the compound of Example I, C. The reaction solution was concentrated in vacuo to give 34 g., m.p. 242°–246°C. The product was dissolved in 500 ml. of MeOH and filtered hot. The filtrate was reduced to a volume of 300 ml. then chilled. The product was collected by filtration, washed with ether and oven-dried (110°C) to yield 22 g. m.p. 252°–254°C.

Anal. Calcd. for $C_{25}H_{30}N_4O_2.HCl$: C, 65.99; H, 6.87; N, 12.32. Found : C, 65.88; H, 6.85; N, 12.28.

EXAMPLE XLV

9-[3,4-di(2-pentyloxy)anilino]-7-methyl-1-H-imidazo[4,5-f]quinoline Hydrochloride A. o-Di(sec-amyloxy)benzene A mixture of 55 g. (0.5 m ) of catechol, 220 g. of anhydrous $K_2CO_3$ and 100 ml. of dimethylformamide was heated 60 minutes on a steam bath with stirring. Then 151 g. (1.0 m.) of sec-amyl bromide was added and the reaction mixture refluxed overnight. After cooling, the mixture was poured into 2000 ml. of ice water, then acidified with conc. HCl to pH 5.0. The acid solution was extracted four times using a total of 3200 ml. of benzene. The benzene extract was washed with 4 × 500 ml. of 10% NaOH, followed by a wash with 4 × 500 ml. of $H_2O$. After drying over anhydrous $MgSO_4$, the benzene solution was concentrated to dryness in vacuo to yield a dark red oil weighing 90 g.

B. 3,4-di(sec-amyloxy)nitrobenzene

To a mixture of 300 ml. of conc. $HNO_3$ and 300 ml. of $H_2O$ was added dropwise 80 g. (0.32 m.) of o-di(sec-amyloxy)benzene (part A) while maintaining a temperature of 10°C. Stirring was continued for an additional 60 minutes at 10°C, then the solution was poured into 2000 ml. addition was poured into 2000 ml. of ice. The aqueous layer was decanted, and the red oil was dissolved in benzene, dried over anhydrous $MgSO_4$ and concentrated to dryness in vacuo. A chromatographic column 32 inches long with O.D. ¾ inch, was packed with 20 inches of neutral alumina. The crude product was dissolved in a 250 ml. mixture of 50/50 $CHCl_3$ and $CCl_4$. After the solution was placed on the column, it was washed several times with the same solvent mixture. The first fraction was collected and concentrated to dryness in vacuo to yield 10 g. of amber-colored oil.

C. 9-[(3,4-Di(sec-amyloxy)anilino]-7-methyl-1H-imidazo[4,5-f]quinoline Hydrochloride A mixture of 10 g. (0.035 m.) of 3,4-di(sec-amyloxy)nitrobenzene (part B) and 100 ml. of ethanol was reduced with hydrogen over one-quarter teaspoon of Raney active nickel catalyst in water. A hydrogen uptake of 7.0 psi. was recorded (calcd. 9.0 psi.). The catalyst was removed by filtration and the filtrate refluxed overnight with 7.6 g. ( 0.035 m.) of the compound of Example I, C. After concentrating to dryness in vacuo the yellow residue was recrystallized from 100 ml. of MeOH to give 19 g. Another recrystallization from 500 ml. of nitromethane gave 8.83 g. m.p. 249°–252°C.

Anal. Calcd. for $C_{27}H_{34}N_4O_2.HCl$: C, 67.13; H, 7.30; N, 11.60. Found: C, 67.39; H, 7.22; N, 11.91.

EXAMPLE XLVI 9-(2,5-Diethoxyanilino)-7-methyl-1H-imidazo[4,5-f]quinoline Hydrochloride A mixture of 30 g. (0.142 m.) of 2,5-diethoxynitrobenzene and 200 ml. of ethanol was reduced with hydrogen over one-half teaspoon of Raney active nickel catalyst in water. A hydrogen uptake of 37 psi. was recorded (calcd. 35.7 psi.). The catalyst was removed by filtration. After adding 30.8 g. (0.142 m.) of the compound of Example I, C. to the filtrate, the reaction mixture was stirred and refluxed overnight. The solution was concentrated in vacuo to give 41 g. m.p. 266°–268°C. A yield of 36 g., m.p. 276°–278° with decomposition, was obtained following a recrystallization from 800 ml. of MeOH.

Another recrystallization from MeOH gave m.p. 273°–275°.

Anal. Calcd for $C_{21}N_{22}N_4O_2.HCl$: C, 63.23; H, 5.81; N, 14.05; Cl, 8.89. Found : C, 62.76; H, 5.83; N, 13.79; Cl, 8.59.

EXAMPLE XLVII 9-(2,5-Dimethoxyanilino)-7-methyl-1H-imidazo[4,5-f]quinoline Hydrochloride Hemihydrate A mixture of 40 g. (0.184 m.) of the compound of Example I, C., 282 g. (0.184 m.) of 2,5-dimethoxyaniline and 500 ml. of ethanol was heated at reflux with stirring overnight. The reaction was concentrated to dryness in vacuo. The product was recrystallized from 800 ml. of MeOH, to give 28 m.p. 258°–293°C. A second recrystallization from 1000 ml. of MeOH gave m.p. 257°–260°C.

Anal. Calcd. for $C_{19}H_{18}N_4O_2.HCl.½H_2O$: C, 60.08; H, 5.31; N, 14.75; Cl, 9.33. Found : C, 59.67; H, 5.45; N, 14.80; Cl, 9.44.

EXAMPLE XLVIII 9-(4-Chloro-4,5-dimethoxyanilino)-7-methyl-1H-imidazo[4,5-f]quinoline Hydrochloride A mixture of 18.5 (0.085 m.) of the compound of Example I, C., 16 g. (0.085 m.) of 4-chloro-2,5-dimethoxyaniline and 250 ml. of ethanol was refluxed with stirring overnight. The solution was concentrated to dryness in vacuo. The crude product was recrystallized from 1000 ml. of MeOH to give 21.5 g., m.p. 274°–277°C.

Anal. Calcd. for $C_{19}H_{17}ClN_4O_2.HCl$: C, 56.30; H, 4.48; N, 13.83; Cl, 17.50. Found : C, 55.97; H, 4.44; N, 13.82; Cl, 17.32, 17.38.

EXAMPLE XLIX 9-(2-Ethoxy-5-methoxyanilino)-7-methyl-1H-imidazo[4,5-f]quinoline Hydrochloride Hydrate A. 2-Nitro-4-methoxyphenol A mixture of 168 g. (0.93 m.) of 3-nitro-p-anisidine, 130 g. of KOH and 1500 ml. of $H_2O$ was refluxed with stirring overnight. The solution was acidified with conc. HCl, keeping the temperature below 20°C. The crude product was collected by filtration washed with $H_2O$ and air-dried to give 279 g. m.p. 74°–76°C. A recrystallization from 2000 ml. of ethanol yields 106 g. m.p.76°–78°C.

B. 2-Ethoxy-5-methoxynitrobenzene

A mixture of 84.5 g. (0.5 m.) of 2-nitro-4-methoxyphenol (part A), 338 g. of $K_2CO_3$ and 1200 ml. of dimethylformamide was heated on a steam bath for 60 minutes, then there was added dropwise, 76.7 ml. (108.98 g. 1.0 m.) of ethyl bromide. The mixture was heated and stirred overnight, then poured into 5 liters of ice water. The product was collected by filtration, washed with $H_2O$ and air-dried to give 92 g. m.p. 37°–39°C.

C. 9-(2-Ethoxy-5-methoxyanilino)-7-methyl-1H-imidazo[4,5-f]quinoline Hydrochloride Hydrate A mixture of 19.72 g. (0.1 m.) of 2-ethoxy-5-methoxynitrobenzene (part B) and 200 ml. of ethanol was reduced with hydrogen over one-half teaspoon of Raney active nickel catalyst in water. A hydrogen uptake of 18.5 psi. was recorded (calcd. 20.1 psi.). The catalyst was removed by filtration and the filtrate refluxed overnight with 21.7 g. (0.1 m.) of the compound of Example I, C. The solution was concentrated in vacuo and the yellow residue recrystallized from ethanol to yield 13 g. m.p. 260°–270°.

Anal. Calcd. for $C_{20}H_{20}N_4O_2 \cdot HCl \cdot H_2O$: C, 59.62; H, 5.75; N, 13.91; Cl, 8.80. Found: C, 59.40; H, 5.49; N, 13.72; Cl, 9.07.

EXAMPLE L 9-(5-Ethoxy-2-methoxyanilino)-7-methyl-1H-imidazo[4,5-f]quinoline Hydrochloride A. p-Methoxyphenyl acetate To 1500 ml. of acetic anhydride was added portionwise 248 g. (2.0 m) of p-methoxyphenol. Following the addition, the solution was heated on a steam bath for 3 hours, then poured into 5 liters of ice water. The solvents were removed by distillation to give an amber colored liquid weighing 273 g.

B. 4-Methoxy-3-nitrophenyl acetate

To a mixture of 270 g. (1.62 m.) of p-methoxyphenyl acetate (part A) and 772 ml. of HOAc was added dropwise 77.5 ml. of fuming $HNO_3$ maintaining a temperature of 5° to 10°C. Stirring was continued for 60 minutes at 5° to 10°C following the addition, then the solution was poured into 6 liters of ice. The orange semisolid was collected by filtration and washed with cold water. The crude product was recrystallized from 1000 ml. of ethanol to give 61 g., m.p. 93°–97°C.

C. 4-Methoxy-3-nitrophenol

A mixture of 61 g. (0.29 m.) of 4-methoxy-3-nitrophenyl acetate (part B) and 34.68 g. (0.87 g. (0.87 m.) of NaOH in 500 ml. of $H_2O$ was stirred and heated on a steam bath for 2 hours. The reaction solution was acidified with 87 ml. of conc. HCl, keeping the temperature below 20°C. The acid solution was extracted three times using a total of 1500 ml. of benzene. The combined benzene extracts were dried over anhydrous $MgSO_4$, filtered and concentrated in vacuo to give 33 g. m.p. 78°–80°.

D. 2-Nitro-4-ethoxyanisole

A mixture of 16.9 g. (0.1 m.) of 4-methoxy-3-nitrophenol (part C), 68 g. of $K_2CO_3$ and 240 ml. dimethylformamide was heated 60 minutes on a steam bath with stirring. Then 15.2 ml. (21.8 g. 0.2 m.) of ethyl bromide was added dropwise and the reaction mixture was further heated with stirring overnight. After cooling the mixture was poured into ice water. The brown solid was collected by filtration, washed with water and air-dried to give 19 g. m.p. 33°–36°C. The crude product was recrystallized from 700 ml. of MeOH to give 17g. m.p. 34°–37°C.

E. 9-(5-Ethoxy-2-methoxyanilino)-7-methyl-1H-imidazo[4,5-f]quinoline Hydrochloride A mixture of 19 g. (0.096 m.) of 2-nitro-4-ethoxyanisole (part D) and 250 ml. of ethanol was shaken with hydrogen over one-half teaspoon of Raney active nickel catalyst in water. A pressure drop of 24 psi. was recorded (calcd. 25.7 psi.). The catalyst was removed by filtration and the filtrate refluxed overnight with 209 g. (0.098 m.) of the compound of Example I, C. The reaction solution was chilled and the solid collected by filtration, washed with ether and air-dried to give 24 g. m.p. 265°–267°C. The crude product was recrystallized from 800 ml. of MeOH to yield 18 g. m.p. 278°–279°C.

Anal. Calcd. for $C_{20}H_{20}N_4O_2 \cdot HCl$: C, 62.41; H, 5.50; N, 14.56; Cl, 9.21. Found: C, 62.47; H, 5.52; N, 14.65; Cl, 9.15.

EXAMPLE LI 9-(4-Chloro-2,5-diethoxyanilino)-7-methyl-1H-imidazo[4,5-f]quinoline Hydrochloride A mixture of 24.6 g. (0.1 m.) of 4-chloro-2,5-diethoxynitrobenzene and 250 ml. of ethanol was reduced with hydrogen using one-half teaspoon of Raney active nickel catalyst in water. The hydrogen uptake was 24 psi. (calc. 25.8 psi.). The catalyst was removed by filtration and the filtrate refluxed and stirred overnight with 21.7 g. (0.1 m.) of the compound of Example I, C. The reaction mixture was concentrated in vacuo to give 46 g. The product was recrystallized from 1500 ml. of MeOH then the filtrate was concentrated to 750 ml. and chilled. The product was filtered, washed with ether and oven-dried (100°C) to yield 35 g. m.p. 280-282°C.

Anal. Calcd. for $C_{21}H_{21}ClN_4O_2 \cdot HCl$: C, 58.20; H, 5.12; N, 12.93; Cl, 16.36. Found: C, 57.78; H, 5.21; N, 12.84; Cl, 16.10.

EXAMPLE LII 9-(5-Chloro-2,4-dimethoxyanilino)-7-methyl-1H-imidazo[4,5-f]quinoline Hydrochloride Hydrate A mixture of 40 g. (0.184 m.) of the compound of Example I, C., 346 g. (0.184 m.) of 5-chloro-2,4-dimethoxyaniline and 500 ml. of ethanol was refluxed with stirring overnight. The solvents were removed by distillation and the crude product dissolved in 3000 ml. of MeOH. The MeOH filtrate was concentrated to one-half its volume, chilled and filtered to yield 13 g. m.p. 400°.

Anal. Calc. for $C_{19}H_{17}ClN_4O_2 \cdot HCl \cdot H_2O$: C, 53.91; H, 4.76; N, 13.24; Cl, 16.76. Found: C, 53.75; H, 4.52; N, 13.17; Cl, 17.16.

EXAMPLE LIII 9-(3,4-5-Trimethoxyanilino)-7-methyl-1H-imidazo[4,5-f]quinoline Hydrochloride A mixture of 12.5 g. (0.068 m.) of 3,4,5-trimetoxyaniline, 14.8 g. (0.068 m.) of the compound of Example I, C. and 250 ml. of ethanol was refluxed with stirring overnight. The reaction mixture was concentrated in vacuo to give 27.5 g. m.p. 287°–289°C. The product was dissolved in 1500 ml. of MeOH, charcoal added, then filtered. The MeOH filtrate was concentrated to a volume of 500 ml and chilled. The product was collected by filtration, washed with ether and oven-dried (100°C) to yield 16.5 g.m.p. 288°–289°C.

Anal. Calcd. for $C_{20}H_{20}N_4O_3 \cdot HCl$: C, 59.92; H, 5.28; N, 13.98; Cl, 8.85. Found: C, 60.13; H, 5.21; N, 13.98; Cl, 8.76.

EXAMPLE LIV

7-Methyl-9-(2,4,5-triethoxyanilino)imidazo[4,5-f]quinoline Hydrochloride

A solution of 12.7 g. (0.05 m.) of 2,4,5-triethoxynitrobenzene in 200 ml. of ethanol was shaken with $H_2$ over 1 g. of 5% Pd/C containing 50% $H_2O$. A pressure drop of 13 psi. (calcd. 13 psi.) in one hr. was recorded. The catalyst was filtered and 10.8 g. (0.05 m.) of the compound of Example I, C. was added to the filtrate. This solution was heated under reflux for 18hr.

then cooled in an ice bath. The crystalline product was filtered and recrystallized from 300 ml. of ethanol to given 9.0 g. of yellow needles, m.p. 158°–170° with elimination of water (after drying at 100° in vacuo).

Anal. Calcd. for $C_{23}H_{26}N_4O_3 \cdot HCl \cdot 1½ H_2O$: C, 58.78; H, 6.43; N, 11.92. Found: C, 58.50; H, 6.37; N, 11.78.

EXAMPLE LV 9-(p-Acetylanilino)-7-methyl-1H-imadazo[4,5-f]quinoline Hydrochloride A mixture of 40 g. (0.184 m.) of the compound of Example I, C., 24.9 g. (0.184 m.) of p-aminoacetophenone and 500 ml. of ethanol was refluxed, with stirring overnight. The solution was concentrated to dryness in vacuo. The crude product was dissolved in 2500 ml. of MeOH, charcoal added, then filtered. The MeOH filtrate was concentrated to a volume of 1000 ml. then chilled. The product was collected by filtration, washed with ether and oven-dried (100°C) to give 47.5 g. m.p. 333°–336°C. A second recrystallization from 1500 ml. of MeOH, followed by concentration of the filtrate yielded 34 g. m.p. 338°–340°C.

Anal. Calcd. for $C_{19}H_{16}N_4O \cdot HCl$: C, 64.68; H, 4.86; N, 15.88; Cl, 10.05. Found: C, 64.34; H, 4.60; N, 15.77; Cl, 9.86.

EXAMPLE LVI 9-(m-Acetylanilino)-7-methyl-1H-imidazo[4,5-f]quinoline Hydrochloride Hemihydrate A mixture of 13.5 g. (0.1 m.) of 3-aminoacetophenone, 21.7 g. (0.1 m.) of the compound of Example I, C. and 500 ml. of ethanol was heated at reflux overnight with stirring. The solution was concentrated in vacuo to give 30 g. m.p. 156°–223°C. The crude product was recrystallized from 1000 ml. of MeOH, followed by concentration of the filtrate to the cloud point. The product was oven-dried (100°C) to yield 24 g. m.p. 225°–228°, completely 251°C.

Anal. Calcd. for $C_{19}H_{16}N_4O \cdot HCl \cdot ½H_2O$: C, 63.07; H, 5.01; N, 15.49; Cl 9.80. Found: C, 63.51; H, 4.81; N, 15.45; Cl, 10.56.

EXAMPLE LVII 9-(p-Propionylanilino)-7-methyl-1H-imidazo[4,5-f]quinoline Hydrochloride A mixture containing 14.9 g. (0.1 m) of p-aminopropiophenone 21.7 g. (0.1 m.) of the compound of Example I, C. and 500 ml. of ethanol was refluxed with stirring overnight. It was then concentrated in vacuo to give 34 g. m.p. 287°–289°, complete 320°C. The crude product was recrystallized from 1000 ml. of MeOH to yield 27 g.m.p. softens 318°, melts 328°–330°C.

Anal. Calcd. for $C_{20}H_{18}N_4O \cdot HCl$: C, 65.48; H, 5.22; N, 15.28; Cl, 9.67. Found: C, 65.55; H, 5.35; N, 15.32; Cl, 9.33.

EXAMPLE LVIII 9-(p-Butyrylanilino)-7-methyl-1H-imidazo[4,5-f]quinoline Hydrochloride Hemihydrate A mixture of 16.3 g. (0.1 m) of 4-aminobutyrophenone, 21.7 g. (0.1 m) of the compound of Example I, C. and 500 ml. of ethanol was refluxed overnight. The solution was concentrated in vacuo to dryness. The soft, yellow solid was dissolved in 300 ml. of MeOH and filtered. The MeOH filtrate was evaporated to a volume of 50 ml. then chilled. The product was filtered, washed with ether and oven-dried (110°C) to give 24 g. m.p. 209°–230°C. A second recrystallization from MeOH yielded 22 g., m.p. 205°–235°C.

Anal. Calcd. for $C_{21}H_{20}N_4O \cdot HCl \cdot 1/2H_2O$: C, 64.69; H, 5.69; N, 14.37. Found: C, 64.94; H, 5.59; N, 14.79.

EXAMPLE LIX 9-(p-Anisidino)-7-methyl-2-phenyl-1H-imidazo[4,5-f]quinoline Hydrochloride Hemihydrate A. 2,4-Dinitrophenylbenzamide To a solution of 73.2 g. (0.4 m.) of 2,4-dinitroaniline in 400 ml. of pyridine with stirring and slight warming was added 56.2 g. (0.4 m.) of benzoyl chloride in about 10 min.; the temperature rose from 40° to 50°. Then the dark solution was heated at reflux for 2½ hours. After standing overnight, the yellow solid was collected, washed with $H_2O$ until no pyridine odor was detectable. This 90 g. of crude product was recrystallized from about 2.1 of $CH_3CN$ to yield 44 g. (38%) of yellow product melting at 201°–205°.

B. 2-Phenyl-5-aminobenzimidazole

A mixture of 44 g. (0.153 m.) of 2,4-dinitrophenylbenzamide in 800 ml. of ethanol together with 6 g. of 5% Pd/C containing 50% $H_2O$ was subjected to reduction. Absorption stopped after 60.5 lb. of uptake of hydrogen (theory = 61.5 lb.) in 2½ hour. The reduction mixture was warmed on steam bath with the addition of about 2½ l of ethanol. The mixture was then filtered hot and crystalline needles separated from the filtrate. This product was collected, washed with ethanol, ether and airdried; m.p. 218°–220°. Concentration of the filtrate yielded more solid. The solids were combined and suspended in 250 ml. of $H_2O$ with the addition of 25 ml. of conc. HCl. The mixture was then heated on the steam bath for 1½ hours. After cooling, the reaction mixture was diluted with $H_2O$ to give a dark solution which, upon neutralization with conc. $NH_4OH$, yielded 30 g. (94%) of tan solid after washing with $H_2O$ and drying at 100°. It decomposed at 235°–250°.

C. Ethyl 3-[5-(2-phenylbenzimidazoylamino)]crotonate

A mixture of 275 g. (1.32 m.) of 2-phenyl-5-aminobenzimidazole, 171 g. (1.32 m.) of ethyl acetoacetate, 200 g. of anhydrous calcium sulfate, 13 ml. of glacial HOAc and 3000 ml. of ethanol was refluxed overnight. After filtration the solution was concentrated in vacuo until a solid remained. Another run was made in the same manner and the products combined to give a total yield of 861 g.

D. 7-Methyl-2-phenyl-9-imidazo[4,5-f]quinolinol

To 8000 ml. of boiling Dowtherm [R] was added 430 g. (1.34 m.) of ethyl 3-[5-(2-phenylbenzimidazoylamino)]crotonate. The reaction was heated at reflux for 90 min. then allowed to cool to room temperature. The crystalline solid was triturated in acetone, filtered and air-dried to give 745 g. m.p. 147°–172°. The crude product was recrystallized from 3000 ml. of dimethylformamide. The yield after oven-drying (100°) was 69 g., m.p. 332°–335° with decomposition. By diluting the dimethylformamide filtrate with $H_2O$, another 188 g. was obtained, m.p. 197°–230° with decomposition, which was recrystallized from 700 ml. of dimethylformamide to yield 50 g. m.p. 332°–336° with decomposition.

Anal. Calcd. for $C_{17}H_{13}N_3O$: C, 74.16; H, 4.76; N, 15.27. Found: C, 73.79; H, 4.68; N, 15.27.

E. 9-Chloro-7-methyl-2-phenylimidazo[4,5-f]quinoline

To a mixture of 88 g. (0.32 m.) of D. and 293 ml. (481 g. 3.2 m.) of $POCl_3$ was added slowly 586 ml. of dimethylformamide. Following the completion of the addition, stirring was continued overnight at room temperature. It was then poured into 4 liters of ice. The crude product was precipitated by the addition of 1200 ml. $NH_4Oh$ to pH 8.0. It was collected by filtration, washed with $H_2O$ and air-dried to give 154 g. m.p. 136°–250°C, slow decomposition. After dissolving the crude product in 5 liters of MeOH, the MeOH filtrate was concentrated to a volume of 750 ml. and chilled. The yield after oven-drying (100°C) was 41 g. A second recrystallization from 2000 ml. of MeOh and followed by concentration to one-half its volume yielded 28 g.

Anal. Calcd. for $C_{17}H_{12}ClN_3$: C, 69.51; H, 4.12; N, 14.31; Cl, 12.07. Found: C, 69.38; H, 4.27; N, 14.32; Cl, 12.22.

F. 9-(p-Anisidino)-7-methyl-2-phenyl-1H-imidazo[4,5-f]quinoline Hydrochloride Hemihydrate A mixture of 17.5 g. (0.06 m.) of E., 7.4 g. (0.06 m.) of p-anisidine and 250 ml. of dimethylformamide was refluxed with stirring overnight. The reaction mixture was chilled, filtered, washed with ether and air-dried to give 23 g. m.p. 215°–315°C. The crude product was recrystallized from 1000 ml. of ethanol to yield 17 g.

Anal. Calcd. for $C_{24}H_{20}N_4O.HCl.1/2 H_2O$: C, 67.58; H, 5.21; N, 13.16; Cl, 8.33. Found: C, 67.40; H, 5.53; N, 13.21; Cl, 8.00.

EXAMPLE LX 9-(p-Anisidino)-7-ethyl-1H-imidazo[4,5-f]quinoline Hydrochloride

A. Ethyl 3-(5-Benzimidazolyamino)-2-ethylcrotonate

A mixture of 34 g. (0.208 m.) of 5-nitrobenzimidazole and 450 ml. of ethanol was shaken with hydrogen over one-half teaspoon of Raney active nickel catalyst in water. A pressure drop of 40 psi was recorded (calcd. 41.7 psi). The catalyst was removed by filtration and the filtrate refluxed overnight with 30 g. (0.208 m.) of ethyl propionylacetate, 100 g. of anhydrous calcium sulfate and 0.2 ml. of HOAc. The anhydrous calcium sulfate was filtered off, and the ethanol filtrate concentrated in vacuo to dryness. The residual oil was recrystallized from ethanol, followed by concentration to one-half its volume to yield 38 g. m.p. 161°–167°C.

B. 7-Ethyl-9-imidazo[4,5-f]quinolinol

To 500 ml. of boiling Dowtherm $^{(R)}$ was added 38 g. (0.15 m.) of ethyl 3-(5-benzimidazolylamino)-2-ethylcrotonate. The reaction was heated at reflux for another 60 minutes, then allowed to cool to room temperature. The solid was collected by filtration, washed with Dowtherm $^{(R)}$, acetone, then air-dried to give 35 g., m.p. 309°–317°C. The crude product was recrystallized from 200 ml. of dimethylformamide, with charcoal, to yield 27 g. m.p. 334°–335°C.

C. 9-Chloro-7-ethylimidazo[4,5-f]quinoline

To a mixture of 27 g. (0.127 m.) of 7-ethyl-9-imidazo[4,5-f]quinoline and 116.4 ml. (195 g. 1.27 m.) of $POCl_3$ was added dropwise 232 ml. of dimethylformamide. The brown mixture was allowed to stir overnight at room temperature then poured into 1000 ml. of ice. The solution was basified to pH 8 using 1000 ml. of conc. $NH_4OH$, keeping the temperature below 20°C. It was then filtered, washed with $H_2O$ and airdried to give 25 g. The crude product was recrystallized from 400 ml. of ethanol, filtering hot to remove the insolubles, and concentrated in vacuo to give 13.4 g.

D. 9-(p-Anisidino)-7-ethyl-1H-imidazo[4,5-f]quinoline Hydrochloride

A mixture of 13 g. (0.058 m.) of 9-chloro-7-ethylimidazo[4,5-f]quinoline (part C), 14.3 g. (0.12 m.) of p-anisidine and 250 ml. of ethanol was refluxed with stirring overnight. The solution was concentrated to dryness in vacuo. The crude product was dissolved in 100 ml. of ethanol. The ethanol filtrate was concentrated to a volume of 200 ml. then chilled. The product was collected by filtration, washed with ether and oven dried (100°C) to yield 13 g. m.p. 307°–310°C.

Anal. Calcd. for $C_{19}H_{18}N_4C.HCl$: C, 64.31; H, 5.40; N, 15.79; Cl, 9.99. Found: C, 63.92; H, 5.46; N, 15.48; Cl, 9.56.

EXAMPLE LXI 9-(p-Anisidino)-7-phenyl-1H-imidazo[4,5-f]qunioline Hydrochloride A. Ethyl 3-(5-Benzimidazolylamino)cinnimite A solution of 900 ml. of ethanol and 82 g. (0.5 mole) of 5-nitrobenzimidazole with 4 g. of 5% Pd/C, 50% $H_2O$ catalyst was reduced on the Parr Apparatus. A pressure drop of 104 psi. was observed (calcd. 100). After the reduction stopped, the bottom was removed from the apparatus, and the catalyst filtered. Then 96 g. (0.5 mole) of ethyl benzoylacetate, 20 g. of anhydrous calcium sulfate and 0.5 ml. of HOAc were added to the filtrate. The solution was refluxed for 2 hours and filtered. The filtrate was concentrated to a dark sticky resin. Crystallization was induced by scratching. The product after cooling was filtered, washed with ethanol and air-dried. The product weighed 55 g. m.p. 188°–190°C.

B. 7-Phenyl-1H-imidazo[4,5-f]quinolin-9-ol

Into a 1000 ml. three-necked flask equipped with a thermometer and heated with a mantle, 300 ml. of Dowtherm $^{(R)}$ was heated to boiling, then 30 g. of A. was added. The solution was boiled for 10 minutes. The flask was removed from the mantle and allowed to cool. The product was filtered and washed with fresh Dowtherm $^{(R)}$, then acetone, and air-dried. The product weighed 10 g. m.p. >300°C. Four more runs were made. All five runs combined into one large sample containing 58 g. This sample was recrystallized from dimethylformamide. The product weighed 43 g. m.p. 318°–320°C.

C. 9-Chloro-7-phenylimidazo[4,5-f]quinoline

To a mixture of 121 g. (0.46 m.) of B. and 424 ml. (712 g. 4.6 m.) of $POCl_3$ was added dropwise over 3 hr., 848 ml. of dimethylformamide. The yellow mixture was allowed to stir overnight then poured into 5 liters of ice. The yellow precipitate was collected by filtration, washed with cold $H_2O$ and air-dried to give 161 g. Following a trituration in 500 ml. of 2N NaOH solution, the product was filtered, washed with $H_2O$ and oven-dried (100°C) to yield 118 g. m.p. 229°–400°C, slow decomposition.

Anal. Calcd. for $C_{16}H_{10}ClN_3$: C, 68.70; H, 3.60; N, 15.02; Cl, 12.68. Found: C, 69.04; H, 3.63; N, 15.07; Cl, 12.59.

D.  9-(p-Anisidino)-7-phenyl-1H-imidazo[4,5-f]quinoline Hydrochloride

A mixture of 27.98 g. (0.1 m.) of C., 12.3 g. (0.1 m.) of p-anisidine and 200 ml. of dimethylformamide was refluxed with stirring overnight. The reaction mixture was chilled, filtered and air-dried to give 49 g. The crude product as recrystallized from 1000 ml. of ethanol, with charcoal, then concentrated to one-half its volume and chilled. A second recrystallization from 250 ml. of dimethylformamide yielded 19 g. It was then stirred in hot water, filtered and oven-dried (100°C) to give 17 g.

Anal. Calcd. for $C_{23}H_{18}N_4O.HCl$: C, 68.57; H, 4.75; N, 13.91; Cl, 8.60. Found: C, 68.81; H, 4.72; N, 13.97; Cl, 7.24.

EXAMPLE LXII 9-(p-Anisidino)-2,7-dimethyl-1H-imidazo[4,5-f]quinoline Hydrochloride A. Ethyl 3-[5-(2-Methylbenzimidazolyl)amino]crotonate To a mixture of 90 g. (0.49 m.) of 5-amino-2-methylbenzimidazole hydrochloride in 1500 ml. of MeOH and 50 ml. of $H_2O$ was added portionwise 150 g. of $NaHCO_3$. The mixture was refluxed for 60 minutes, then cooled and filtered. The filtrate was heated on a steam bath until the MeOH had boiled off then cooled and filtered to remove the solid (mostly NaCl). After the addition of ethanol to the filtrate, the mixture was again heated on a steam bath to a low volume, cooled and filtered. The filtrate was concentrated in vacuo to give a dark, glassy solid. After adding 300 ml. of benzene, 200 ml. of ethanol, 65 g. (0.5 m.) of ethyl acetoacetate and a quantity of anhydrous calcium sulfate, the mixture was refluxed 3 hours. It was then filtered hot and concentrated in vacuo to a dark gummy residue. The crude product was dissolved in 200 ml. of ethanol and precipitated with 300 ml. of $H_2O$ to yield 54 g., m.p. 140°–144°C of white needles.

B. 2,7Dimethyl-1H-imidazo[4,5-f]quinolin-9-ol

To 1500 ml. of boiling Dowtherm was added portionwise 105 g. (0.406 m.) of ethyl 3-[5-(2-methylbenzimidazolyl)amino]crotonate. The reaction mixture was heated at reflux for 30 minutes, then allowed to cool to room temperature. The brown solid was collected by filtration, washed with Dowtherm, acetone and then air-dried to give 70 g, m.p. >400°C. The crude product was recrystallized from 2500 ml. of dimethylformamide to yield 37.5 g. m.p. >400°C.

C. 9-Chloro-2,7-dimethylimidazo[4,5-f]qunioline

To a mixture of 31 g. (0.146 m.) of 2,7-dimethyl-1H-imidazo[4,5-f]-quinolin-9-ol and 1336 ml. (223 g. 1455 m.) of $POCl_3$ was added dropwise 267.2 ml. of dimethylformamide. The mixture was stirred overnight at room temperature, then poured into 1000 ml. of ice. The solution was basified to pH 8.0 using conc. $NH_4OH$, keeping the temperature below 20°C. It was then filtered, washed with $H_2O$ and air-dried. The crude product was recrystallized from 2000 ml. of MeOH, and concentrated in vacuo to yield 338 g. m.p. 314°–330°C.

D.  9-(p-Anisidino)-2,7-dimethyl-1H-imidazo[4,5-f]quinoline Hydrochloride

A mixture of 18.5 g. (0.08 m.) of 9-chloro-2,7-dimethylimidazo [4,5-f]-quinoline, 9.85 g. (0.08 m.) of p-anisidine and 300 ml. of ethanol was refluxed, with stirring, overnight. The solution was concentrated in vacuo to give 27 g. m.p. 307°–311°C. Recrystallization from 300 ml. of MeOH yielded 13 g. m.p. 317°–318°C.

Anal. Calcd. for $C_{19}H_{18}N_4O.HCl$: C, 64.31; H, 5.40; N, 15.79; Cl, 9.99. Found: C, 64.46; H, 5.47; N, 15.77; Cl, 9.92.

EXAMPLE LXIII 9-(p-Anisidino)-7-methyl-1H-imidazo[4,5-f]quinoline-2-one Hydrochloride A. 5(or 6)-Nitro-2-benzimidazolinone A solution of 153 g. (1.0 mole) of 4-nitro-o-phenylenediamine and 70 g. (1.2 mole) of urea in 1 l. of dimethylformamide was heated carefully to boiling; evolution of ammonia began as the boiling point was approached. The solution was refluxed for 3¾ hours, at which time the condenser became plugged with sublimed urea. Charcoal was added, the solution was boiled 5 minutes and filtered. Two liters of hot water was added with stirring. After cooling in ice the brown crystalline product was filtered, washed with cold water, then with 1N Hcl until the washings were colorless, then with water and dried in the 60° oven to yield 169 g. (95%), m.p. 315°–322°.

B. Ethyl 3-(2-oxobenzimidazolyl)crotonate

A mixture of 90 g. (0.5 m.) of A. and 1000 ml. of ethanol was shaken with hydrogen over one teaspoon of Raney active nickel catalyst in water. A pressure drop of 94 psi. was recorded (calcd. 100.5 psi.). The catalyst was removed by filtration and the filtrate was refluxed overnight with 65 g. (0.5 m.) of ethyl acetoacetate, 150 g. of anhydrous calcium sulfate and 0.5 ml. of HOAc. The calcium sulfate was removed by filtration and the filtrate concentrated in vacuo to give 92 g. The crude product was triturated in 4000 ml. of MeOH, filtered hot and oven-dried (100°C) to yield 32 g. m.p. darkens 264°, melts >400°C.

C. 9-Hydroxy-7-methylimidazo[4,5-f]quinolin-2-one Hydrate

To 500 ml. of boiling Dowtherm (R) was added portionwise, 27 g. (0.104 m) of ethyl 3-(2-oxobenzimidazolyl)crotonate. The reaction mixture was heated at reflux for 60 minutes, then allowed to cool to room temperature. The solid was collected by filtration, washed with Dowtherm, acetone and then air-dried. The crude product was triturated in hot dimethylformamide, followed by a tituration in hot water to yield 19 g. m.p. melts >400°C.

Anal. Calcd. for $C_{11}H_9N_3O_2.H_2O$: C, 56.65; H, 4.75; N, 18.02. Found: C, 56.53; H, 4.54; N, 17.59.

D.  9-Chloro-7-methylimidazo[4,5-f]quinolin-2-one Tetartohydrate

To a mixture of 88 g. (0.378 m.) of C. and 347 ml. (5.79 g. 3.78 m.) of $POCl_3$ was added 694 ml. of dimethylformamide. Stirring was continued overnight at room temperature, then the mixture was poured into 3000 ml. of ice. The mixture was basified to pH 6 using 28% $NH_4OH$, keeping the temperature less than 20°C. The brown precipitate was collected by filtration, washed with $H_2O$ and oven-dried (110°C) to give 338 g. m.p. >400°C. The crude product was recrystallized from 6000 ml. of dimethylformamide, with charcoal. The dimethylformamide filtrates were concentrated in vacuo to near dryness. The residue was triturated in ethanol to yield 73 g. m.p. >400°C.

E. 9-(p-Anisidino)-7-methylimidazo[4,5-f]quinoline-2-one Hydrochloride

A mixture of 23.8 g. (0.1 m.) of 9-chloro-7-methylimidazo[4,5-f]quinolin-2-one tetartohydrate, 12.3 g. (0.1 m.) of p-anisidine and 500 ml. of ethanol was refluxed overnight. The reaction mixture was concentrated to dryness in vacuo. The residue was dissolved in 2500 ml. of MeOH, then filtered. The MeOH filtrate was concentrated to dryness in vacuo, then the residue was triturated with ether. Recrystallization from MeOH yielded 10 g. m.p. 275°–400°C.

Anal. Calcd. for $C_{18}N_{16}N_4O_2 \cdot HCl$: C, 60.59; H, 4.80; N, 15.70. Found: C, 60.68; H, 4.92; N, 15.42.

EXAMPLE LXIV

9-[(p-Methoxybenzyl)amino]-7-methyl-1H-imidazo[4,5-f]quinoline Hydrochloride hydrate A stirred mixture of the compound of Example I, C. (22 g. 0.1 mole) and p-methoxy-benzylamine (14 g. 0.1 mole) in 200 ml. of dimethylformamide was refluxed for 6 hours. The reaction solution was stripped in vacuo to give 35 g. (98%) of pale yellow solid. Recrystallization from $CH_3OH$/ether gave m.p. 250°–255°C.

Anal. Calcd. for $C_{19}H_{18}N_4O \cdot HCl \cdot \frac{1}{4}H_2O$: C, 61.95; H, 5.61; N, 15.21. Found: C, 61.70; H, 5.83; N, 15.38.

EXAMPLE LXV

9-Cyclohexylamino-7-methyl-1H-imidazo[4,5-f]quinoline Hydrochloride

A solution of 22 g. (0.1 m.) of the compound of Example I, C., and 10 g. (0.1 m.) cyclohexylamine in 200 ml. of dimethylformamide was heated under reflux for 18 hours and filtered hot. The crystalline product which separated on cooling was filtered, washed with a little cold dimethylformamide then ether and air-dried to give 17 g. Recrystallization from 300 ml. of ethanol and 300 ml. of ether gave an analytical sample as white needles, m.p. 174°–178°.

Anal. Calcd. for $C_{17}H_{20}N_4 \cdot HCl \cdot H_2O$: C, 60.97; H, 6.92; N, 16.73. Found: C, 60.54; H, 7.08; N, 16.73.

EXAMPLE LXVI 9-(p-Phenylanilino)-7-methyl-1H-imidazo[4,5-f]quinoline Hydrochloride Tetartohydrate A 500 ml. 3-neck, r.b. flask fitted with stirrer, condenser and thermometer was charged with the compound of Example I, C. (21.7 g. 0.1 mole), 4-biphenylamine (16.9 g. 0.1 mole) and ethanol (300 ml.). The mixture was stirred while heating at reflux overnight. The reaction mixture was concentrated to dryness by rotary evaporator and the residue was collected and dried to yield 47.9 g. (124%) tan crystals, m.p. 338°–355°C. A portion (37 g.) of the crude product was dissolved in methanol (800 ml.), treated with charcoal and filtered while hot. Ether was added until the filtrate became turbid and then chilled. The crystals were collected by filtration and dried to yield 19.6 g. yellow crystals, m.p. 335°–352°C (dec.). Recrystallization from methanol gave m.p. 343°–357°C (dec.).

Anal. Calcd. for $C_{23}H_{18}N_4 \cdot HCl \cdot \frac{1}{2}H_2O$: C, 70.58; H, 5.02; N, 14.32. Found: C, 70.61; H, 5.00; N, 14.29.

EXAMPLE LXVII 9-(4-Methyl-3-nitroanilino)-7-methyl-1H-imidazo[4,5-f]quinoline Hydrochloride A mixture of 10.85 g. (0.05 m.) of the compound of Example I, C., 7.6 g. (0.05 m.) of 4-methyl-3-nitroaniline and 500 ml. of ethanol was refluxed overnight. The reaction mixture was concentrated in vacuo to give 38 g. of crude product. It was then dissolved in 6000 ml. of MeOH and filtered hot. The MeOH filtrate was concentrated in vacuo to yield 27 g., m.p. 344°–345°C.

Anal. Calcd. for $C_{18}H_{15}N_5O_2 \cdot HCl$: C, 58.46; H, 4.36; N, 18.94. Found: C, 57.98; H, 4.46; N, 18.60.

EXAMPLE LXVIII 9-(4-Chloro-2-methylanilino)-7-methyl-1H-imidazo[4,5-f]quinoline Hydrochloride A solution of 22 g. (0.1 m.) of the compound of Example I, C. and 14 g. (0.1 m.) of 4-chloro-2-methylaniline in 200 ml. of dimethylformamide was heated under reflux for 17 hours and filtered hot. The crystalline product which separated on cooling was filtered, washed with cold dimethylformamide, then ether and air-dried, giving 22 g. of straw-colored product. Recrystallization from 550 ml. of ethanol gave 14 g. m.p. 199°–206°.

Anal. Calcd. for $C_{18}H_{15}ClN_4 \cdot HCl$: C, 60.17; H, 4.49; N, 15.60. Found: C, 59.82; H, 4.46; N, 15.53.

EXAMPLE LXIX 9-(3-Chloro-4-ethylanilino)-7-methyl-1H-imidazo[4,5-f]quinoline Hydrochloride A. Preparation of 3-Chloro-4-ethylaniline:

A 500 ml. reduction bottle was charged with 3-chloro-4-ethylnitrobenzene (41 g. 0.222 mole) and dimethylformamide (200 ml.). The mixture was shaken with hydrogen over 1 teaspoon Raney active nickel catalyst in water. A hydrogen uptake of 53 psi. was recorded (calcd. 57.6 psi.). The catalyst was removed from the warm mixture by filtration and the filtrate was used in Part B.

B. Preparation of title compound

A 500 ml. 3-neck, r.b. flask fitted with stirrer, condenser and thermometer was charged with the filtrate from Part A, the compound of Example I, C. (44.3 g. 0.204 mole) and an additional 100 ml. dimethylformamide and the mixture was heated at reflux overnight while stirring. The near solution was chilled and the crystals were collected by filtration. The solid was washed with ether (ca. 300 ml.). Crop I was dried at 60°C to yield 46.8 g. straw colored crystals, m.p. 258°–272°C. The ether filtrate was concentrated to near dryness and chilled. Crop II was collected and dried to yield 7.2 g. tan crystals, m.p. 256°–270°C. The reaction filtrate was concentrated to about 200 ml. diluted with ether (100 ml.) and chilled. Crop III was collected and dried to yield 6.8 g. tan crystals, m.p. 120°–130°C. The crude product (Crops, I, II and III) was dissolved in isopropanol (ca. 2800 ml.) and filtered while hot. The filtrate was chilled and the crystals collected by filtration and dried at 60°C to yield 25.3 g. light yellow crystals, m.p. 283°–287° C. The filtrae was concentrated to 1400 ml. by rotary evaporator and chilled. The crystals were collected and dried to yield 8.9 g. light yellow crystals, m.p. 282°–287°C.

Anal. Calcd. for $C_{19}H_{17}ClN_4 \cdot HCl$: C, 61.13; H, 4.86; N, 15.01. Found: C, 61.06; H, 4.88; N, 14.98.

EXAMPLE LXX 9-(3-Chloro-4-n-butylanilino)-7-methyl-1H-imidazo[4,5-f]quinoline Hydrochloride Hemihydrate A. Preparation of 3-chloro-4-n-butylaniline:

A 500 ml. reduction bottle was charged with a 2-chloro-4-nitro-n-butyl-benzene (24 g. 0.113 mole) and dimethylformamide (200 ml.). The mixture was shaken with hydrogen over 1 teaspoon Raney active nickel catalyst in water. A hydrogen uptake of 25 psi. was recorded (calcd. 30.6 psi.). The catalyst was removed by filtration and a small portion of the filtrate was diluted with water (25 ml.) and transferred to a separatory funnel. The oil was extracted with benzene and the organics were dried over magnesium sulfate. The salt was removed by filtration and the filtrate was concentrated to dryness. The aniline was identified by IR.

B. A 500 ml. 3-neck, r.b. flask fitted with stirrer, condenser and thermometer was charged with the remainder of the filtrate from part A, the compound of Example I, C.(20.9 g. 0.0962 mole) and an additional 100 ml. dimethylformamide. The mixture was stirred overnight while heating at 110°C. The solution was chilled and the crystals were collected by filtration and dried at 60°C to yield 23 g. off white crystals, m.p. 260°–268°C. The filtrate was concentrated to 150 ml. by rotary evapaorator and chilled. Crop II was collected and dried to yield 3.9 g. light yellow crystals, m.p. 238°–251°C. Both crops were dissolved in isopropanol (600 ml.) and filtered while hot. The filtrate was chilled and the crystals were collected and dried at 60°C to yield 13.2 g. light yellow crystals, m.p. 273°–276°C.

Anal. Calcd. for $C_{21}H_{21}ClN_4 \cdot HCl \cdot \frac{1}{2}H_2O$: C, 61.46; H, 5.65; N, 13.66. Found: C, 61.43; H, 5.34; N, 13.55.

EXAMPLE LXXI 9-(3-Chloro-4-fluoroanilino)-7-methyl-1H-imidazo[4,5-f]quinoline Hydrochloride A mixture of 14.5 g. (0.1 m.) of 3-chloro-4-fluoroaniline, 21.7 g. (0.1 m.) of the compound of Example I, C. and 500 ml. of ethanol was refluxed overnight with stirring. It was then chilled, filtered and the product washed with ether and air-dried to give 25 g. The crude product was recrystallized from 1500 ml. of MeOH to yield 17 g.

Anal. Calcd. for $C_{17}H_{12}ClFN_4 \cdot HCl$: C, 56.21; H, 3.61; N, 15.40. Found: C, 56.76; H, 3.50; N, 15.20.

EXAMPLE LXXII

9-[3-Chloro-4-(1-pyrrolidinyl)anilino]-7-methyl-1H-imidazo[4,5-f]quinoline Hydrochloride Hemihydrate A. Preparation of 3-Chloro-4-(1-pyrrolidinyl)nitrobenzene:

A mixture of 3,4-dichloronitrobenzene (38.4 g. 0.2 mole) and pyrrolidine (28.4 g. 0.4 mole) was heated at 100°–115°C in a 250 ml. glass lined pressure bottle for 9 hours. The reaction product was ground in a mortar with water (ca. 250 ml.) and filtered. The dark brownish-yellow solid was dissolved in ethanol (450 ml.) and filtered while hot. The filtrate was chilled and the crystals collected by filtration and dried to yield 36 g. (79.7%) dark yellow crystals, m.p. 87°–92°C.

Anal. Calcd. for $C_{10}H_{11}ClN_2O_2$: C, 52.99; H, 4.89; N, 12.36. Found: C, 52.92; H, 4.93; N, 12.66.

B. Preparation of 3-chloro-4-(1-pyrrolidinyl)aniline:

A 500 ml. reduction bottle was charged with 3-chloro-4-(1-pyrrolidinyl)nitrobenzene (35 g. 0.155 mole) and ethanol (200 ml). The mixture was shaken with hydrogen over ½ teaspoon Raney active nickel catalyst in water. A hydrogen uptake of 37 psi. was recorded (calcd. 39.9 psi.).The catalyst was removed by filtration and the filtrate was concentrated to dryness to obtain 20 g. dark brown liquid which was used in part C.

C. Preparation of title compound:

A 500 ml. 3-neck, r.b. flask fitted with stirrer, condenser and thermometer was charged with 3-chloro-4-(1-pyrrolidinyl)aniline (20 g. 0.102 mole), the compound of Example I, C. (22.2 g. 0.102 mole) and ethanol (350 ml.) and the mixture was stirred overnight while heating at reflux. The reaction mixture was concentrated to dryness by rotary evaporator. The residue was collected and partially dried at 100°C. A small sample (2.0 g.) was dissolved in methanol (100 ml.), treated with charcoal and filtered while hot. Ether (400 ml.) was added until the filtrate remained turbid and was then chilled. The crystals were collected by filtration and dried to yield 1.0 g. m.p. 331°–332°C. Recrystallization gave m.p. 318°–320°C.

Anal. Calcd. for $C_{21}H_{20}ClN_5 \cdot HCl \cdot \frac{1}{2}H_2O$: C, 59.58; H, 5.24; N, 16.54 Found: C, 59.51; H, 5.16; N, 16.66

EXAMPLE LXXIII 9-(p-Phenylazoanilino)-7-methyl-1H-imidazo[4,5-f]quinoline Hydrochloride A solution of 11.7 g. (0.05 m.) of p-phenylazoaniline hydrochloride in 500 ml. of ethanol was adjusted to pH 7.0 with 28% $NH_4OH$. After the addition of 11 g. (0.05 m.) of the compound of Example I, C., the mixture was refluxed overnight. It was chilled, filtered, washed with ether and airdried to give 22 g. The crude product was recrystalled from MeOH to yield 17 g.

Anal. Calcd. for $C_{23}H_{18}N_6 \cdot HCl$: C, 66.58; H, 4.62; N, 20.26. Found: C, 66.53; H, 4.64; N, 20.34.

EXAMPLE LXXIV 9-(4-Chloro-2-Methoxyaniline)-7-methyl-1H-imidazo[4,5-f]quinoline Hydrochloride A mixture of 15.76 g. (0.1 m.) of 4-chloro-2-anisidine, 21.7 g. (0.1 m.) of the compound of Example I, C. and 500 ml. of ethanol was refluxed overnight. The solution was chilled, filtered, washed with ether and air-dried to give 29 g. Another recrystallization from 500 ml. of dimethylformamide, filtering hot, yielded 20 g. m.p. darkens 285°, melts 295°–297°C.

Anal. Calcd. for $C_{18}H_{15}ClN_4O \cdot HCl$: 57.61; H, 4.30; N, 14.93. Found: C, 57.33; H, 4.28; N, 14.82.

EXAMPLE LXXV 9-(3,4-Methylenedioxyanilino)-7-methyl-1H-imidazo[4,5-f]quinoline Hydrochloride A mixture of 10 g. (0.06 m.) of 3,4-methylenedioxynitrobenzene and 200 ml. of ethanol was reduced with hydrogen over one-half teaspoon of Raney active nickel catalyst in water. A hydrogen uptake of 11.5 psi. was recorded (calcd. 15.5 psi.). The catalyst was removed by filtration and the filtrate refluxed overnight with 13 g. (0.06 m.) of the compound of Example I, C. The solution was reduced to a volume of 200 ml., then chilled, filtered, washed with ether and air-dried to give 20 g. The crude product was dissolved in 1500 ml. of MeOH, charcoal added, then filtered. The MeOH filtrate was concentrated to a volume of 300 ml. then chilled, filtered, and oven-dried to yield 15 g. m.p. slow decomposition 357°–400°C.

Anal. Calcd. for $C_{18}H_{14}N_4O_2 \cdot HCl$: C, 60.93; H, 4.26; N, 15.79. Found: C, 60.65; H, 4.25; H, 15.78.

EXAMPLE LXXVI

9-(3,4-Dipentoxyanilino)-7-methyl-1H-imidazo[4,5-f]quinoline Hydrochloride Tetartohydrate Ten grams (0.033 m.) of 3,4-dipentoxyaniline hydrochloride was dissolved in 500 ml. of ethanol, then neutralized with 28% $NH_4OH$. After adding 7.2 g. (0.033 m.) of the compound of Example I, C., the mixture was refluxed with stirring overnight. Concentration in vacuo gave 17 g. The crude product was recrystallized from 300 ml. of MeOH to yield 16 g. m.p. 236°–238°C.

Anal. Calcd. for $C_{27}H_{34}N_4O_2 \cdot HCl \cdot \frac{1}{2}H_2O$: C, 66.51; H, 7.34; N, 11.60. Found: C, 66.63; H, 7.24; N, 11.57.

EXAMPLE LXXVII

9-(3,4-Diisoamyloxyanilino)-7-methyl-1H-imidazo[4,5-f]quinoline Hydrochloride Tetartohydrate A. 3,4-Diisoamyloxynitrobenzene To a mixture of 300 ml. of conc. $HNO_3$ and 300 ml. of $H_2O$ was added dropwise 90 g. (0.36 m.) of o-diisoamyloxybenzene while maintaining a temperature of 19°–21°C. Stirring was continued for an additional 60 minutes at 19°–21°C, then the solution was poured into 3 liters of ice. The crude product was collected by filtration, washed with cold $H_2O$ and airdried to give 90 g. It was recrystallized from 300 ml. of MeOH to give 25.5 g. A chromatographic column, 32 inches long with O.D. ¾inch, was packed with 20 inches of neutral alumina. The 25 g. of crude product was dissolved in a 250 ml. mixture of 50/50 $CHCl_3$ and $CCl_4$. After the mixture was placed on the column, it was washed several times with the same solvent mixture. The first fraction, very light yellow in color, was collected and concentrated to dryness in vacuo to yield 15 g. m.p. 44°–47°C.

B. 9-(3,4-Diisoamyloxyanilino)-7-methyl-1H-imidazo[4,5-f]quinoline Hydrochloride Tetarthydrate A mixture of 15 g. (0.05 m.) of 3,4-diisoamylnitrobenzene and 100 ml. of ethanol was shaken with hydrogen over one-quarter teaspoon of Raney active nickel catalyst in water. A hydrogen uptake of 13.5 psi. was recorded (calcd. 12.9 psi.). The catalyst was removed by filtration and the filtrate refluxed overnight with 11 g. (0.05 m.) of the compound of Example I, C. The solution was chilled, filtered, washed with ether and air-dried to give 25 g. m.p. 258°–261°C. The crude product was recrystallized from 250 ml. of ethanol to yield 15 g. m.p. 265°–266°C.

Anal. Calcd. for $C_{27}H_{34}N_4O_2 \cdot HCl \cdot \frac{1}{2}H_2O$: C, 66.51; H, 7.34; N, 11.49 Found: C, 66.56; H, 7.31; N, 11.69.

EXAMPLE LXXVIII

9-(4-Chloro-2,5-dibutoxyanilino)-7-methyl-1H-imidazo[4,5-f]quinoline Hydrochloride A mixture of 30 g. (0.1 m.) of 4-chloro-2,6-dibutoxy-1-nitrobenzene and 250 ml. of ethanol was shaken with hydrogen over one-half teaspoon of Raney active nickel catalyst in water. A pressure drop of 22 psi. was recorded (calcd. 25.8 psi.). The catalyst was removed by filtration and the ethanol filtrate refluxed overnight with 22 g. (0.1 m.) of the compound of Example, I, C. The solution was concentrated in vacuo to give 63 g. The crude product was recrystallized from 300 ml. of MeOH to yield 40 g. m.p. 241°–243°C.

Anal. Calcd. for $C_{25}H_{29}ClN_4O_2 \cdot HCl$: C, 61.35; H, 6.18; N, 11.45. Found: C, 61.32; H, 6.12; N, 11.51.

EXAMPLE LXXIX

9-[p-(2-Diethylaminoethoxy)anilino]-7-methyl-1H-imidazo[4,5-f]quinoline Trihydrochloride Monohydrate A. 2-Diethylaminoethyl-p-nitrophenyl Ether Hydrochloride To 118 g. (0.74 mole) of sodium p-nitrophenylate in 750 ml. of dimethylformamide was added 100 g. (0.74 mole) of 2-diethylaminoethyl chloride and the mixture was heated on a steam bath with stirring for 3 hours. The solution was cooled and diluted with 500 ml. of anhydrous ether and was treated with an ether-hydrogen chloride solution to pH 3. The product was collected by filtration and was washed with ether to give a white solid melting at 163°–165° (corr.) in a yield of 171 g. (98%).

Anal. Calcd. for $C_{12}H_{18}N_2O_3 \cdot HCl$: C, 52.45; H, 6.97; N, 10.20. Found: C, 52.29; H, 7.00; N, 10.38.

B. 2-Diethylaminoethyl p-Aminophenyl Ether Dihydrochloride

A mixture of 168 g. (0.7 mole) of A., and 30 g. of 5% palladium on carbon (50% wet), in 1 l of ethanol was hydrogenated on a Parr apparatus in a 2 l bottle. The theoretical amount of hydrogen was taken up in 2 hours and the catalyst was removed by filtration. The filtrate was treated with an ether-hydrogen chloride solution to pH 3. The mixture was cooled and the product was collected as pale yellow needles melting at 206°–208° in a yield of 147 g. (86%). Recrystallization from ethanol raised the melting point to 210°–211°.

Anal. Calcd. for $C_{12}H_{20}N_2O \cdot 2HCl$: C, 51.25; H, 7.89; N, 9.96. Found: C, 51.09; H, 8.09; N, 9.62.

C. 9-[p-(2-Diethylaminoethoxy)anilino]-7-methyl-1H-imidazo[4,5-f]quiinoline Trihydrochloride Monohydrate.

A stirred mixture of the compound of Example I, C. (22 g. 0.1 mole) and the free base of B. (42 g. 0.2 mole) in 200 ml. of dimethylformamide was refluxed for 6 hours. The reaction mixture was stripped in vacuo to give a tar. The tar was recrystallized twice from ethanolic HCl/ether to yield 33 g. (64%), m.p. 206°C.

Anal. Calcd. for $C_{23}H_{27}N_5O \cdot 3HCl \cdot H_2O$: C, 53.44; H, 6.24; N, 13.55; Cl, 20.58. Found: C, 53.38; H, 6.30; N, 13.55; Cl, 21.73.

EXAMPLE LXXX

9-(p-n-Butylanilino)-7-phenyl-1H-imidazo[4,5-f]quinoline Hydrochloride

A 500 ml. 3-neck, r.b. flask fitted with stirrer, condenser and thermometer was charged with the compound of Example LXI, C. (13.95 g. 0.05 mole), p-n-butylaniline (7.45 g. 0.05 mole) and dimethylformamide (300 ml.). The mixture was stirred overnight while heating at 100°C. The reaction solution was concentrated to dryness by rotary evapaorator and the residue was collected and dried at 100°C to yield 19.9 g. (93%) dark brown crystals, m.p. 305°–330°C. A small sample (2.0 g.) was dissolved in methanol (50 ml.) and filtered while hot. Ether (ca. 250 ml.) was added until the solution became turbid and it was then chilled. The crystals were collected by filtration and dried at 100°C overnight to yield 1.0 g. white crystals, m.p. 318°–325°C. Recrystallization yielded a m.p. 324°–326°C.

Anal. Calcd. for $C_{26}H_{24}N_4 \cdot HCl$: C, 72.80; H, 5.87; N, 13.06. Found: C, 72.53; H, 5.84; N, 13.07.

EXAMPLE LXXXI 9-(p-Anisidino)-1H-imidazo[4,5-f]quinoline Hydrochloride Tetartohydrate A. Ethyl 9-Hydroxy-1H-imidazo[4,5-f]quinoline-9-carboxylate An 82 g. portion (0.5 mole) of 5-nitrobenzimidazole in 1 l of ethanol was reduced over 5 g. of 5% palladium-charcoal catalyst containing 50% water. The reduction stopped after a pressure drop of 97 psig. (97%) in 75 min. The catalyst was filtered, 108 g. (0.5 mole) of diethoxymethylenemalonate was added to the filtrate and the solution was boiled in an open flask until about one-half of the solvent had boiled away (ca. 2 hr.). The product set to a solid cake upon cooling. Ethanol containing a little water was added to assist in breaking up the cake and the product was filtered, washed with cold ethanol-$H_2O$ (3:1) and air-dried; yield, 125 g. (83%). A 50 g. portion of this anil was added to 500 ml. of boiling Dowtherm over a 3-4 min. period and boiling was continued 4 min. longer. After cooling to room temperature the product was filtered, washed with Dowtherm, then benzene and air-dried; 44 g. of crude product was obtained. Extraction of this material with 500 ml. of boiling ethanol gave 22 g., m.p. 315°–316°C.

B. 9-Hydroxyimidazo[4,5-f]quinoline-8-carboxylic Acid

A mixture of 356 g. (1.384 mole) of A. and 3000 ml. of 2N NaOH solution was heated at reflux for 3 hours. The solution was stirred for 1 hour with charcoal, filtered, and acidified with 509 ml. of concentrated HCl. The crude product was collected by filtration, washed with $H_2O$, then acetone, and air-dried to give 380 g. m.p. 304°–308°.

After dissolving 40 g. of the crude product in 3000 ml. of dimethylformamide, with charcoal, the filtrate was diluted with 3000 ml. of $H_2O$. It was then filtered, washed with acetone and oven-dried (100°) to give 35.5 g. A second recrystallization from 3000 ml. of dimethylformamide, with charcoal and concentration of the filtrate to a volume of 500 ml. yielded 29 g. m.p. 358°–360°.

Anal. Calcd. for $C_{11}H_7N_3O_3$: C, 57.64; H, 3.08; N, 18.34. Found: C, 57.65; H, 3.05; N, 18.12.

C. 9-Imidazo[4,5-f]quinolinol

A mixture of 254 g. (1.108 mole) of B. and 1400 ml. of quinaldine was heated at reflux for 9 hours while passing nitrogen into the mixture. The brown solid was collected by filtration, washed with benzene and air-dried to give 183 g. It was then suspended in 3000 ml. of $H_2O$, and 150 ml. of conc. HCl added to pH 2.5. After stirring for 60 min. the solution was filtered. The filtrate was chilled to 20°C, and conc. $NH_4OH$ added to a pH 8-pH 9. The brown precipitate was collected by filtration, washed with $H_2O$ and oven-dried (100°C) to yield 182 g. m.p. 366°–368°C.

Anal. Calcd. for $C_{10}H_7N_3O$: C, 64.86; H, 3.81; N, 22.69. Found: C, 64.88; H, 3.82; N, 22.69.

D. 9-Chloroimidazo[4,5-f]quinoline

To a mixture of 150 g. (0.813 mole) of C. and 743 ml. (1244 g. 8,13 mole) of $POCl_3$ was added dropwise over 5 hours, 1486 ml. of dimethylformamide. The brown mixture was allowed to stir overnight at room temperature then slowly poured into 5 liters of ice. The solution was basified to pH 8 using 2800 ml. of conc. $NH_4OH$. It was then filtered, washed with water and air-dried to give 304 g. The crude product was dissolved in 16 liters of MeOH filtered hot to remove the insolubles, and the MeOH filtrate concentrated in vacuo to give 141 g. A second recrystallization from 4000 ml. of MeOH, with charcoal, yielded 82.5 g.

Anal. Calcd. for $C_{10}H_5ClN_3$: C, 59.27; H, 2.49; N, 20.74; Cl, 17.50. Found: C, 58.99; H, 2.99; N, 20.69; Cl, 17.09.

E. 9-(p-Anisidino)-1H-imidazo [4,5-f]quinoline Hydrochloride Tetratohydrate

A mixture of 20.3 g. (0.1 mole) of D., 12.3 g. (0.1 mole) of p-anisidine and 250 ml. of ethanol was refluxed with stirring for 10 hours. The reaction solution was chilled and the solid collected by filtration, washed with ether and air-dried. The crude product was recrystallized from 4000 ml. of ethanol with charcoal to yield 19 g.

Anal. Calcd. for $C_{17}H_{14}N_4O \cdot HCl \cdot ¼H_2O$; C, 61.63; H, 4.72, N, 16.91; Cl, 10.70. Found: C, 61.83; H, 5.08; N, 16.91; Cl, 10.91.

The anthelminitic efficacy of members of the series of compounds of this invention was determined by a method which involves artificially infecting mice with *Hymenolepis nana*. A compound of formula (1) was administered to one group of mice while another group serves as a control. At the end of the treatment period each group was sacrificed, autopsied, and the number of worms in each is counted. The number of worms in the treated group as compared to the number of worms in the untreated group represents the percentage clearance effected by the compound. The results secured for the compounds of this invention are set forth in this fashion: Compound of Example (Dose per os in mg/kg. b.i.d. for three days) (% clearance): I (100) (41); II (100) (72); III (300) (100); IV (300) (98); V (300) (100); VI (50) (90); VII (300) (100); VIII (100) (100); IX (100) (100); X (100) (84); XI (300 ) (100); XII (100) (100); XIII (50) (53); XIV (100) (65); XV (100) (61); XVI (100) (84); XVII (100) (100); XVIII (100) (75); XIX (100) (71); XX (50) (62); XXI (300) (80); XXII (50) (87); XIII (100) (100); XXIV (300)(100); XXV (300) (100); XXVI (25) (77); XXVII (300) (84); XXVII (100) (64); XXIV (100) (100); XXX (100) (66); XXXI (100) (100); XXXII (300) (100); XXXIII (100) (73); XXXIV (100) (100); XXXV (50) (62); XXXVI (100) (81); XXXVII (300) (93); XXXVIII (100) (100); XXXIX (50) (90); XL (100) (73); XLI (50) (84); XLII (50) (94); XLIII (25) (77); XLIV (50) (95); XLV (50) ( 100); XLVI (50) (100); XLVII (100) (100); XLVIII (100) (72); XLIX (100) (100); L (100) (100); LI (50) (100); LII (100) (85); LIII (100) (70); LIV (100) (89); LV (50) (100); LVI (100) (96); LVII (300) (100); VLIII (300) (100); LIX (100) (94); LX (300) (100); LXI (100) (66); LXII (300) (100); LXIII (100) (66); LXIV (300) (60); LXV (300) (81); LXVI (50) (84); LXVII (300) (83); LXVIII (100) (100); LXIX (50) (93); LXX (50) (100); LXXI (100) (82); LXXII (100) (100); LXXIII (100) (100); LXXIV (  300) (100); LXXV (300) (100); LXXVI (300) (100); LXXVII (50) (100); LXXVIII(50) (84); LXXIX (300) (100); LXXX (300) (69) and LXXXI (100) (100).

What is claimed is:

1. The compound 9-(p-phenylazoanilino)-7-methyl-1H-imidazo[4,5-f]quinoline.

* * * * *